US010480385B2

(12) United States Patent
Okamoto et al.

(10) Patent No.: US 10,480,385 B2
(45) Date of Patent: Nov. 19, 2019

(54) APPARATUS FOR MEASURING COMBUSTIBLE-GAS CONCENTRATION, SYSTEM FOR MEASURING COMBUSTIBLE-GAS CONCENTRATION, SYSTEM FOR TREATING EXHAUST GAS, METHOD FOR MEASURING COMBUSTIBLE-GAS CONCENTRATION, AND METHOD FOR DERIVING CONSTANT

(71) Applicant: NGK INSULATORS, LTD., Nagoya-shi, Aichi (JP)

(72) Inventors: Taku Okamoto, Nagoya (JP); Yoshinobu Nakada, Nagoya (JP); Kosuke Monna, Aichi (JP)

(73) Assignee: NGK INSULATORS, LTD., Nagoya (JP)

(*) Notice: Subject to any disclaimer, the term of this patent is extended or adjusted under 35 U.S.C. 154(b) by 84 days.

(21) Appl. No.: 15/673,766

(22) Filed: Aug. 10, 2017

(65) Prior Publication Data
US 2018/0112583 A1    Apr. 26, 2018

Related U.S. Application Data
(60) Provisional application No. 62/411,745, filed on Oct. 24, 2016.

(30) Foreign Application Priority Data
Apr. 27, 2017 (JP) .................................. 2017-88741

(51) Int. Cl.
F01N 13/00 (2010.01)
B01D 53/94 (2006.01)
(Continued)

(52) U.S. Cl.
CPC ........... *F01N 13/008* (2013.01); *B01D 53/30* (2013.01); *B01D 53/9431* (2013.01);
(Continued)

(58) Field of Classification Search
CPC combination set(s) only.
See application file for complete search history.

(56) References Cited

U.S. PATENT DOCUMENTS 7,975,537 B2 * 7/2011 Wang ................. G01N 33/0054
73/114.71
9,823,216 B2 * 11/2017 Wang ................. G01N 27/4075
(Continued)

FOREIGN PATENT DOCUMENTS
JP         4671253 B2      1/2011

*Primary Examiner* — Binh Q Tran
(74) *Attorney, Agent, or Firm* — Global IP Counselors, LLP

(57) ABSTRACT

A apparatus 70 for measuring combustible-gas concentration includes an electromotive force acquisition section 75 configured to acquire information about an electromotive force of a mixed potential cell 55 while a detection electrode 51 is exposed to a target gas, an oxygen concentration acquisition section 76 configured to acquire information about oxygen concentration $p_{O2}$ in the target gas, and a control section 72. The control section 72 derives combustible-gas concentration $p_{THC}$ in the target gas from the acquired information about the electromotive force EMF, the acquired information about the oxygen concentration $p_{O2}$, and the relationship represented by formula (1):

$$\text{EMF} = \alpha \log_a(p_{THC}) - \beta \log_b(p_{O2}) + B \qquad (1)$$

where $\alpha$, $\beta$, and B each represent a constant, and a and b each represent any base (provided that $a \neq 1$, $a > 0$, $b \neq 1$, and $b > 0$).

13 Claims, 8 Drawing Sheets

(51) Int. Cl.
*G01N 27/406* (2006.01)
*G01N 27/407* (2006.01)
*B01D 53/30* (2006.01)
*G01N 27/419* (2006.01)
*F01N 3/20* (2006.01)
*F01N 3/10* (2006.01)
*F01N 3/021* (2006.01)

(52) U.S. Cl.
CPC ..... *B01D 53/9477* (2013.01); *G01N 27/4067* (2013.01); *G01N 27/4074* (2013.01); *G01N 27/4075* (2013.01); *G01N 27/4077* (2013.01); *G01N 27/419* (2013.01); *B01D 53/944* (2013.01); *B01D 53/9418* (2013.01); *B01D 53/9436* (2013.01); *B01D 2255/904* (2013.01); *F01N 3/021* (2013.01); *F01N 3/103* (2013.01); *F01N 3/106* (2013.01); *F01N 3/2066* (2013.01); *F01N 13/009* (2014.06); *F01N 2560/02* (2013.01); *F01N 2560/023* (2013.01); *F01N 2560/025* (2013.01); *F01N 2560/20* (2013.01); *F01N 2570/18* (2013.01); *F01N 2610/02* (2013.01)

(56) References Cited

U.S. PATENT DOCUMENTS

2009/0266142 A1* 10/2009 Wang ................ G01N 33/0054
73/23.32
2011/0048970 A1* 3/2011 Sugaya ................ G01N 27/419
205/781
2016/0356196 A1* 12/2016 Nakano ................... F01N 3/208

* cited by examiner

APPARATUS FOR MEASURING COMBUSTIBLE-GAS CONCENTRATION, SYSTEM FOR MEASURING COMBUSTIBLE-GAS CONCENTRATION, SYSTEM FOR TREATING EXHAUST GAS, METHOD FOR MEASURING COMBUSTIBLE-GAS CONCENTRATION, AND METHOD FOR DERIVING CONSTANT

The present application claims priority from U.S. provisional Patent Application No. 62/411,745 filed on Oct. 24, 2016 and Japanese Patent Application No. 2017-88741 filed on Apr. 27, 2017, the entire contents of which are incorporated herein by reference.

BACKGROUND OF THE INVENTION

1. Field of the Invention

The present invention relates to an apparatus for measuring combustible-gas concentration, a system for measuring combustible-gas concentration, a system for treating an exhaust gas, a method for measuring a combustible-gas concentration, and a method for deriving a constant.

2. Description of the Related Art

Hitherto, apparatuses for detecting combustible-gas concentrations, such as hydrocarbon gases, in target gases, such as exhaust gases of automobiles, have been known. For example, Patent Literature 1 describes an apparatus for measuring combustible-gas concentration with a sensor element including a solid electrolyte and a reference electrode and a detection electrode arranged on the solid electrolyte.

CITATION LIST

Patent Literature

[PTL 1] Japanese Patent No. 4671253

SUMMARY OF THE INVENTION

An electromotive force EMF of a mixed potential cell including a solid electrolyte body and a pair of electrodes is seemingly represented by formula (2). Here, the combustible-gas concentration refers to the carbon-equivalent concentration of a combustible gas in a target gas. However, the inventors have conducted studies and have found that in actual sensor elements, the relationship among an electromotive force EMF, a combustible-gas concentration $p_{THC}$, an oxygen concentration $p_{O2}$, a $H_2O$ concentration $p_{H2O}$, and a $CO_2$ concentration $p_{CO2}$ does not obey formula (2), in some cases. Thus, when the combustible-gas concentration $p_{THC}$ is derived from formula (2) in a mixed potential-type combustible-gas sensor, the combustible-gas concentration in the target gas is not accurately derived, in some cases.

[Math. 1]

$$EMF = \frac{RT}{nF}(K1 \ln p_{THC} - K2 \ln p_{O2} - K3 \ln p_{H2O} - K4 \ln p_{CO2}) + K5 \qquad (2)$$

(Where
EMF: the electromotive force of the mixed potential cell
R: gas constant [J/K·mol)]
T: the temperature of the mixed potential cell [K]
F: the Faraday constant [C/mol]
$p_{THC}$: the combustible-gas concentration in the target gas
$p_{O2}$: the oxygen concentration in the target gas
$p_{H2O}$: the $H_2O$ concentration in the target gas
$p_{CO2}$: the $CO_2$ concentration in the target gas
n: number of electrons n
K1~K5: constants)

The present invention has been accomplished in order to solve these problems and mainly aims to derive combustible-gas concentration in a target gas with higher accuracy.

In the present invention, the following measures are used in order to achieve the above-described main object.

An apparatus according to the present invention, the apparatus for measuring combustible-gas concentration serving as carbon-equivalent concentration of a combustible gas in a target gas with a sensor element includes a mixed potential cell that includes a solid electrolyte body, a detection electrode arranged on the solid electrolyte body, and a reference electrode arranged on the solid electrolyte body, the apparatus includes:

an electromotive force acquisition section configured to acquire information about an electromotive force of the mixed potential cell while the detection electrode is exposed to the target gas;

an oxygen concentration acquisition section configured to acquire information about oxygen concentration in the target gas; and a combustible gas concentration derivation section configured to derive the combustible-gas concentration in the target gas depending on the acquired information about the electromotive force, the acquired information about the oxygen concentration, and a relationship represented by formula (1):

$$EMF = \alpha \log_a(p_{THC}) - \beta \log_b(p_{O2}) + B \qquad (1)$$

(where
EMF: the electromotive force of the mixed potential cell,
$\alpha$, $\beta$, and B: constants,
a and b: any base (provided that a≠1, a>0, b≠1, and b>0),
$p_{THC}$: the combustible-gas concentration in the target gas, and
$p_{O2}$: the oxygen concentration in the target gas).

In the apparatus for measuring combustible-gas concentration, the combustible-gas concentration in the target gas is derived from the information about the electromotive force of the mixed potential cell of the sensor element, the information about the oxygen concentration in the target gas, and the relationship of formula (1). In this way, the use of formula (1) can derive the combustible-gas concentration in the target gas with higher accuracy than that in the case of using formula (2) described above. Here, the derivation of the combustible-gas concentration on the basis of the relationship of formula (1) may be executed by using the relationship of formula (1) and is not limited to the derivation of the combustible gas concentration using formula (1) itself. For example, the combustible-gas concentration may be derived from a formula obtained by modifying formula (1). The relationship among the values of the variables (EMF, $p_{THC}$, and $p_{O2}$) of formula (1) is stored in the form of a map, and the combustible-gas concentration may be derived from the map. The constants $\alpha$, $\beta$, and B are values depending on the sensor element and can be determined by, for example, experiments in advance. Here, "combustible-gas concentration that is the carbon-equivalent concentration of a combustible gas in a target gas" may also be expressed as the carbon-equivalent concentration of a hydrocarbon gas in the target gas.

A system of the present invention for measuring combustible-gas concentration includes the sensor element and the combustible-gas concentration measurement apparatus. Accordingly, the system for measuring combustible-gas concentration has the same effect as the apparatus of the present invention for measuring combustible-gas concentration, i.e., for example, the effect of deriving combustible-gas concentration in a target gas with higher accuracy.

In the system for measuring combustible-gas concentration, the detection electrode may be composed of a Au—Pt alloy as a main component. The Au—Pt alloy is suitable for a main component of the detection electrode because a mixed potential is easily established at the triple phase boundary of the solid electrolyte body and the target gas. In this case, the detection electrode may have a degree of concentration (=amount of Au present [atom %]/amount of Pt present [atom %]) of 0.3 or more, the degree of concentration being measured by at least one of X-ray photoelectron spectroscopy (XPS) and Auger electron spectroscopy (AES). A degree of concentration of 0.3 or more can more reliably establish the mixed potential. The degree of concentration may be 0.1 or more.

In the system of the present invention for measuring combustible-gas concentration, the sensor element may include a heater configured to heat the mixed potential cell to an operating temperature of 450° C. or higher and 600° C. or lower. In the system for measuring combustible-gas concentration, the use of an operating temperature of 450° C. or higher can appropriately activate the solid electrolyte body. In the system for measuring combustible-gas concentration, the use of an operating temperature of 600° C. or lower can inhibit a decrease in the derivation accuracy of the combustible-gas concentration because hydrocarbons in the combustible gas are easily introduced into a reaction field around the detection electrode without being oxidized.

In the system of the present invention for measuring combustible-gas concentration, the sensor element may include a protective layer that covers the detection electrode and has a porosity of 28% or more by volume. In this case, for example, the protective layer of the sensor element can suppress defects of the sensor element, such as the occurrence of cracking in the sensor element due to the adhesion of water in the target gas. The use of the protective layer having a porosity of 28% or more by volume can suppress the fact that hydrocarbon gases having a large number of carbon atoms fail to reach the periphery of the detection electrode, thereby inhibiting a decrease in the derivation accuracy of the combustible-gas concentration.

A system of the present invention for treating an exhaust gas includes any one of the systems for measuring combustible-gas concentration according to the foregoing embodiments, and an exhaust gas path through which an exhaust gas serving as the target gas from an internal combustion engine flows, the sensor element being arranged in the exhaust gas path. Accordingly, the system for treating an exhaust gas has the same effect as the system for measuring combustible-gas concentration, i.e., for example, the effect of deriving combustible-gas concentration in a target gas with higher accuracy.

The system of the present invention for treating an exhaust gas may further include one or more supply sections arranged in the exhaust gas path, the one or more supply sections being configured to supply at least one of urea and ammonia, in which the internal combustion engine may be a diesel engine, and the sensor element may be arranged upstream from the most upstream supply section of the one or more supply sections arranged in the exhaust gas path.

Here, when at least one of urea and ammonia is supplied into the exhaust gas path, ammonia concentration in the target gas is increased to affect the electromotive force of the mixed potential cell of the sensor element. In this system for treating an exhaust gas, the arrangement of the sensor element as described above enables the combustible-gas concentration to be derived in a state in which the apparatus for measuring combustible-gas concentration is affected by ammonia as little as possible.

In the present invention, a method for measuring combustible-gas concentration serving as a carbon-equivalent concentration of a combustible gas in a target gas with a sensor element includes a mixed potential cell that includes a solid electrolyte body, a detection electrode arranged on the solid electrolyte body, and a reference electrode arranged on the solid electrolyte body, the method includes:

an electromotive force acquisition step of acquiring information about an electromotive force of the mixed potential cell while the detection electrode is exposed to the target gas;

an oxygen concentration acquisition step of acquiring information about oxygen concentration in the target gas; and a combustible gas concentration derivation step of deriving the combustible-gas concentration in the target gas from the acquired information about the electromotive force, the acquired information about the oxygen concentration, and a relationship represented by formula (1):

$$\text{EMF} = \alpha \log_a(p_{THC}) - \beta \log_b(p_{O2}) + B \qquad (1)$$

(where

EMF: the electromotive force of the mixed potential cell, $\alpha$, $\beta$, and B: constants, a and b: any base (provided that a≠1, a>0, b≠1, and b>0), $p_{THC}$: the combustible-gas concentration in the target gas, and $p_{O2}$: the oxygen concentration in the target gas).

In the method for measuring combustible-gas concentration, as with the apparatus for measuring combustible-gas concentration, the combustible-gas concentration in the target gas can be derived with higher accuracy from the relationship of formula (1). In the method for measuring combustible-gas concentration, the apparatus for measuring combustible-gas concentration, the system for measuring combustible-gas concentration, and the system for treating an exhaust gas according to various embodiments may be used, and steps of providing these functions may be added.

In the present invention, a method for deriving a constant in a relational formula used to measure combustible-gas concentration serving as carbon-equivalent concentration of a combustible gas in a target gas with a sensor element including a mixed potential cell that includes a solid electrolyte body, a detection electrode arranged on the solid electrolyte body, and a reference electrode arranged on the solid electrolyte body, the method includes:

(a) a step of multiple times of executing electromotive force measurement processing that measures an electromotive force of the mixed potential cell in a state in which the detection electrode is exposed to the target gas while at least one of oxygen concentration and the carbon-equivalent concentration of at least one combustible gas of one or more combustible gases in the target gas is changed, a gas containing oxygen and the one or more combustible gases being used as the target gas; and (b) a step of deriving constants α, β, and B in formula (1) from results of the electromotive force measurement processing executed multiple times:

$$EMF = \alpha \log_a(p_{THC}) - \beta \log_b(p_{O2}) + B \quad (1)$$

(where
EMF: the electromotive force of the mixed potential cell,
α, β, and B: constants,
a and b: any base (provided that a≠1, a>0, b≠1, and b>0),
$p_{THC}$: the combustible-gas concentration in the target gas, and
$p_{O2}$: the oxygen concentration in the target gas).

In the method for deriving a constant, the constants α, β, and B in formula (1) used to derive the combustible-gas concentration can be derived. In step (a), the first electromotive force measurement processing may be executed three times or more while at least one of the oxygen concentration and the carbon-equivalent concentration of at least one combustible gas of the one or more combustible gases in the target gas is changed.

In the method of the present invention for deriving a constant, step (a) may include (a1) a substep of executing the electromotive force measurement processing multiple times at a constant oxygen concentration and different carbon-equivalent concentrations of a particular hydrocarbon in the target gas, the particular hydrocarbon being defined as one or more kinds of hydrocarbons, excluding alkanes, among hydrocarbons having 3 or more carbon atoms, and the target gas being defined as a gas containing the particular hydrocarbon and (a2) a substep of executing the electromotive force measurement processing multiple times at a constant carbon-equivalent concentration of a particular hydrocarbon and different oxygen concentrations in the target gas, the particular hydrocarbon being defined as one or more kinds of hydrocarbons, excluding alkanes, among hydrocarbons having 3 or more carbon atoms, and the target gas being defined as a gas containing the particular hydrocarbon; and step (b) may include (b1) a substep of deriving the constant α in formula (1) from the results of the electromotive force measurement processing executed multiple times in substep (a1) by regarding the carbon-equivalent concentration of the particular hydrocarbon as the combustible-gas concentration prim, (b2) a substep of deriving the constant β from the results of the electromotive force measurement processing executed multiple times in substep (a2) by regarding the carbon-equivalent concentration of the particular hydrocarbon as the combustible-gas concentration $p_{THC}$, and (b3) a substep of deriving the constant B in formula (1) from the derived constants α and β and the results of the electromotive force measurement processing executed one or more times in at least one of substeps (a1) and (a2). In this case, because the electromotive force measurement processing is executed multiple times at a constant oxygen concentration in substep (a1), the constant α is easily derived in substep (b1). Similarly, because the electromotive force measurement processing is executed multiple times at a constant carbon-equivalent concentration of the particular hydrocarbon in substep (a2), the constant β is easily derived in substep (b2). The inventors have found that the degree of the effect (sensitivity) of hydrocarbons, excluding alkanes, having 3 or more carbon atoms on the electromotive force EMF of the mixed potential cell is higher than that of hydrocarbons having 2 or less carbon atoms. Thus, in this method for deriving a constant, because the constants α, β, and B are derived by regarding the carbon-equivalent concentration of the particular hydrocarbon as the combustible-gas concentration $p_{THC}$, the particular hydrocarbon being defined as the one or more kinds of hydrocarbons, excluding alkanes, among hydrocarbons having 3 or more carbon atoms, more appropriate constants can be derived. The "particular hydrocarbon" in substeps (a1) and (b1) may be the same as the "particular hydrocarbon" in substeps (a2) and (b2). Alternatively, at least one hydrocarbon may be different.

In this case, the target gas may not contain a hydrocarbon gas other than the particular hydrocarbon in substep (a1). That is, the hydrocarbon in the target gas may be one or more kinds of hydrocarbons only, excluding alkanes, among hydrocarbons having 3 or more carbon atoms in substep (a1). Similarly, the target gas may not contain a hydrocarbon gas other than the particular hydrocarbon in substep (a2). That is, the hydrocarbon in the target gas may be one or more kinds of hydrocarbons only, excluding alkanes, among hydrocarbons having 3 or more carbon atoms in substep (a2).

In the method of the present invention for deriving a constant, in substep (a1), the particular hydrocarbon may be one or more kinds of hydrocarbons among hydrocarbons that have 3 or more carbon atoms, that have a double bond, and that do not have a triple bond, and in substep (a2), the particular hydrocarbon may be one or more kinds of hydrocarbons among hydrocarbons that have 3 or more carbon atoms, that have a double bond, and that do not have a triple bond. In the method of the present invention for deriving a constant, one or more alkenes having 3 or more carbon atoms may be used as the particular hydrocarbon in substep (a1), and one or more alkenes having 3 or more carbon atoms may be used as the particular hydrocarbon in substep (a2).

In this case, the target gas may not contain a hydrocarbon gas other than the particular hydrocarbon in substep (a1). That is, the hydrocarbon in the target gas may be one or more alkenes only among alkenes having 3 or more carbon atoms in substep (a1). Similarly, the target gas may not contain a hydrocarbon gas other than the particular hydrocarbon in substep (a2). That is, the hydrocarbon in the target gas may be one or more alkenes only among alkenes having 3 or more carbon atoms in substep (a2).

In the method of the present invention for deriving a constant, in substep (a1), the target gas may be a gas containing only a single kind of hydrocarbon, and in substep (a2), the target gas may be a gas containing only a single kind of hydrocarbon. In this case, because the target gas used in each of substeps (a1) and (a2) is easily prepared, the constants α, β, and B can be more easily derived.

DETAILED DESCRIPTION OF THE INVENTION

Figure 1:
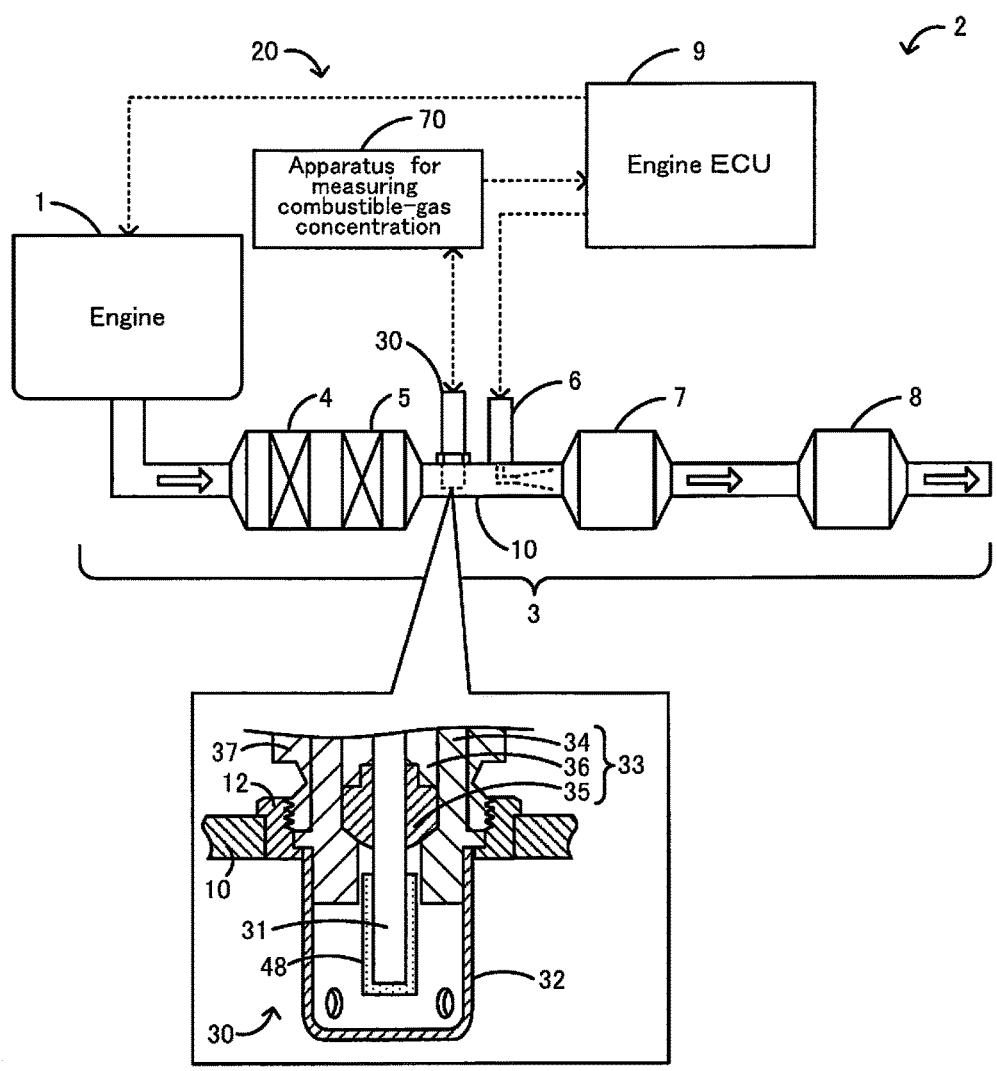
FIG. 1 is an explanatory drawing of a system 2 for treating an exhaust gas of an engine 1.
Figure 2:
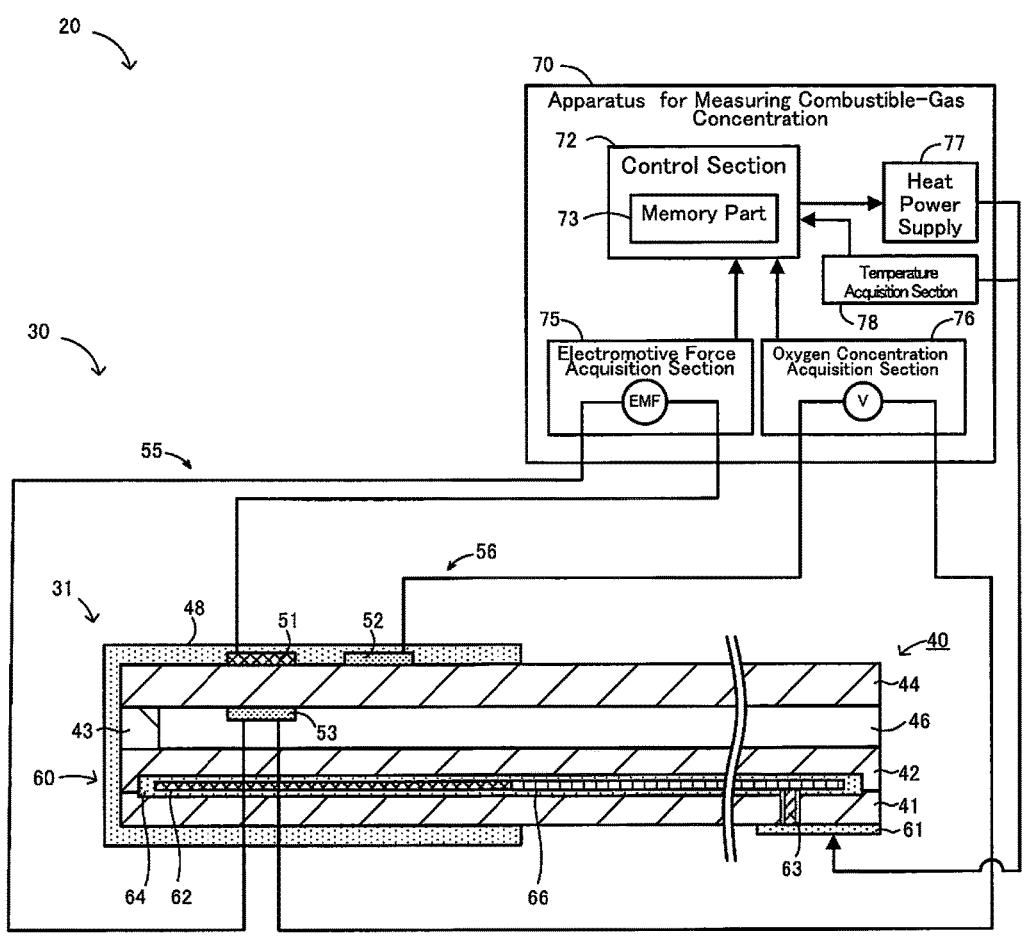
FIG. 2 is an explanatory drawing of a system 20 for measuring combustible-gas concentration.

Embodiments of the present invention will be described below with reference to the drawings. FIG. 1 is an explanatory drawing of a system 2 for treating an exhaust gas of an engine 1. FIG. 2 is an explanatory drawing of a system 20 for measuring combustible-gas concentration.

The system 2 for treating an exhaust gas is a system for treating an exhaust gas serving as a target gas from the engine 1. In this embodiment, the engine 1 is a diesel engine. As illustrated in FIG. 1, the system 2 for treating an exhaust gas includes an exhaust gas path 3 connected to the engine 1 and the system 20 for measuring combustible-gas concentration, the system 20 including a gas sensor 30 arranged in the exhaust gas path 3. In the system 2 for treating an exhaust gas, a diesel oxidation catalyst (DOC) 4, a diesel particulate filter (DPF) 5, the gas sensor 30, an injector 6, a selective catalytic reduction (SCR) 7, and an ammonia slip catalyst (ASC) 8 are arranged, in this order, from the upstream side toward the downstream side of the exhaust gas. The DOC 4 is one of oxidation catalysts included in the system 2 for treating an exhaust gas and converts hydrocarbons (HCs) and CO in the exhaust gas into water and carbon dioxide for detoxification. The DPF 5 traps PM in the exhaust gas. The exhaust gas passing through the DPF 5 flows through a pipe 10. The gas sensor 30 is attached to the pipe 10. The injector 6 is a device configured to inject at least one of ammonia and a substance capable of forming ammonia (for example, urea) into an exhaust pipe to supply the at least one of ammonia and the substance to the SCR 7. In this embodiment, the injector 6 injects urea, and the injected urea is hydrolyzed to form ammonia. The injector 6 is attached to the pipe 10. The gas sensor 30 attached to the pipe 10 is arranged on the upstream side of the exhaust gas path 3 and arranged upstream from the injector 6. The SCR 7 is arranged on the downstream side of the pipe 10. The SCR 7 decomposes nitrogen oxides (NOx) in the exhaust gas into harmless $N_2$ and $H_2O$ by reduction using ammonia supplied from the injector 6 into the exhaust pipe. The ASC 8 is arranged downstream from the SCR 7. ASC 8 is one of the oxidation catalysts included in the system 2 for treating an exhaust gas and is also referred to as a "downstream DOC" with respect to the DOC 4 (upstream DOC). The ASC 8 decomposes excessive ammonia in the exhaust gas passing through the SCR 7 into harmless $N_2$ and $H_2O$ by oxidation. The exhaust gas passing through the ASC 8 is released into, for example, air.

The system 20 for measuring combustible-gas concentration includes the gas sensor 30 and an apparatus 70 for measuring combustible-gas concentration, the apparatus 70 being electrically connected to the gas sensor 30. The gas sensor 30 is a combustible-gas sensor configured to generate an electrical signal depending on the concentration of the combustible gas contained in the target gas passing through the DOC 4 and the DPF 5 in the pipe 10. The gas sensor 30 also functions as an oxygen sensor configured to generate an electrical signal depending on the concentration of oxygen in the target gas and serves as a multi-sensor. The apparatus 70 for measuring combustible-gas concentration derives combustible-gas concentration in the target gas from the electrical signal generated by the gas sensor 30 and transmits the resulting data to an engine ECU 9. The engine ECU 9 controls the amount of fuel injected into the engine 1 in such a manner that the detected combustible-gas concentration approaches zero. The engine ECU 9 also controls the amount of urea injected from the injector 6 into the exhaust pipe. The system 20 for measuring combustible-gas concentration will be described in detail below.

As illustrated in FIG. 1, the gas sensor 30 is fixed in the pipe 10 in such a manner that the central axis of the gas sensor 30 is perpendicular to the flow of the target gas in the pipe 10. The gas sensor 30 may be fixed in the pipe 10 in such a manner that the central axis of the gas sensor 30 is perpendicular to the flow of the target gas in the pipe 10 and is tilted at a predetermined angle (for example, 45°) with respect to the vertical direction (an up and down direction of FIG. 1). As illustrated in the enlarged cross-sectional view of FIG. 1, the gas sensor 30 includes a sensor element 31, a protective cover 32 that covers and protects the front end side (the lower end side in FIG. 1) of the sensor element 31, which is an end side of the sensor element 31 in the longitudinal direction, an element fixing portion 33 that encapsulates and fix the sensor element 31, and a nut 37 fitted to the element fixing portion 33. The one end side of the sensor element 31 is covered with a porous protective layer 48.

The protective cover 32 is a cylindrical cover with a closed bottom, the cylindrical cover covering one end of the sensor element 31. Although a single-layer cover is used in FIG. 1, for example, two-or-more-layer cover including an inner protective cover and an outer protective cover may be used. The protective cover 32 has holes through which the target gas is allowed to flow into the protective cover 32. The one end of the sensor element 31 and the porous protective layer 48 are arranged in a cavity surrounded by the protective cover 32.

The element fixing portion 33 includes a cylindrical main metal fitting 34, a ceramic supporter 35 encapsulated in an inner through-hole of the main metal fitting 34, and a compact 36 that is encapsulated in the inner through-hole of the main metal fitting 34 and that is formed of a ceramic powder composed of, for example, talc. The sensor element 31 is located on the central axis of the element fixing portion 33 and extends through the element fixing portion 33 in the longitudinal direction. The compact 36 is compressed between the main metal fitting 34 and the sensor element 31. Thus, the compact 36 seals the through-hole in the main metal fitting 34 and fixes the sensor element 31.

The nut 37 is fixed coaxially with the main metal fitting 34 and has an external thread portion on an outer periphery thereof. The external thread portion of the nut 37 is fitted with a fitting member 12 that is welded to the pipe 10 and that has an internal thread portion on an inner periphery thereof. Thus, the gas sensor 30 can be fixed to the pipe 10 while the one end side of the sensor element 31 and the protective cover 32 protrude into the pipe 10.

The sensor element 31 will be described with reference to FIG. 2. The cross-sectional view of the sensor element 31 of FIG. 2 illustrates a sectional view taken along the central axis of the sensor element 31 in the longitudinal direction (cross section taken in the up and down direction of FIG. 1). The sensor element 31 includes a base 40 composed of an oxygen-ion-conducting solid electrolyte, a detection electrode 51 and an auxiliary electrode 52 arranged on the side of an end (the lower end of FIG. 1 and the left end of FIG. 2) of the sensor element 31 and on the upper surface of the base 40, a reference electrode 53 arranged inside the base 40, and a heater portion 60 that adjusts the temperature of the base 40.

The base 40 has a plate-like structure in which four layers, i.e., a first substrate layer 41, a second substrate layer 42, a spacer layer 43, and a solid electrolyte layer 44, are stacked, in this order, from the bottom in FIG. 2, each of the layers being formed of an oxygen-ion-conducting solid electrolyte layer composed of, for example, zirconia ($ZrO_2$). A solid electrolyte used to form these four layers is a dense, gastight material. The periphery of a portion of the base 40 in the protective cover 32 is exposed to the target gas introduced into the protective cover 32. A reference gas introduction cavity 46 is provided between an upper surface of the second substrate layer 42 and a lower surface of the solid electrolyte layer 44 in the base 40, a side portion of the cavity being defined by a side surface of the spacer layer 43. The reference gas introduction cavity 46 has an opening portion on the other end side (right end side of FIG. 2) remote from the one end side of the sensor element 31. For example, air is introduced into the reference gas introduction cavity 46, air serving as a reference gas used to measure combustible-gas concentration and oxygen concentration. Each of the layers of the base 40 may be formed of a substrate containing 3% to 15% by mole yttria ($Y_2O_3$) (yttria-stabilized zirconia (YSZ) substrate) serving as a stabilizer.

A detection electrode 51 is a porous electrode arranged on an upper surface of the solid electrolyte layer 44 of the base 40 in FIG. 2. The detection electrode 51, the solid electrolyte layer 44, and the reference electrode 53 form a mixed potential cell 55. In the mixed potential cell 55, a mixed potential (electromotive force EMF) is generated in the detection electrode 51, depending on the concentration of a predetermined gas component in the target gas. The value of the electromotive force EMF between the detection electrode 51 and the reference electrode 53 is used to derive the combustible-gas concentration serving as the carbon-equivalent concentration of a combustible gas in the target gas. The detection electrode 51 is composed of, as a main component, a material that establishes a mixed potential depending on the combustible-gas concentration and that has detection sensitivity to the combustible-gas concentration. The detection electrode 51 may be composed of a noble metal, such as gold (Au), as a main component. The detection electrode 51 is preferably composed of a Au—Pt alloy as a main component. The term "main component" used here refers to a component contained in a largest amount present (atm %, atomic percent) with respect to the total amount of components contained. The detection electrode 51 preferably has a degree of concentration (=amount of Au present [atom %]/amount of Pt present [atom %]) of 0.1 or more, more preferably 0.3 or more, the degree of concentration being measured by at least one of X-ray photoelectron spectroscopy (XPS) and Auger electron spectroscopy (AES). A degree of concentration of 0.3 or more can more reliably establish the mixed potential. The degree of concentration of the detection electrode 51 refers to the degree of surface concentration on a surface of noble metal particles of the detection electrode 51. The amount of Au present [atom %] is determined as the amount of Au present on the surfaces of the noble metal particles of the detection electrode 51. Similarly, the amount of Pt present [atom %] is determined as the amount of Pt present on the surfaces of the noble metal particles of the detection electrode 51. With regard to the surfaces of the noble metal particles, a surface (for example, an upper surface in FIG. 2) of the detection electrode 51 or a fracture surface of the detection electrode 51 may be used. For example, in the case where the surface (the upper surface in FIG. 2) of the detection electrode 51 is exposed, the degree of concentration can be measured on the surface; hence, the measurement may be performed by XPS. The degree of concentration may also be measured by AES. In the case where the detection electrode 51 is covered with the porous protective layer 48 as described in this embodiment, the fracture surface (fracture surface in the up and down direction of FIG. 2) of the detection electrode 51 is subjected to measurement by XPS or AES to determine the degree of concentration. A higher degree of concentration results in a smaller amount of Pt present on the surface of the detection electrode 51, thereby inhibiting the decomposition of hydrocarbon gas in the target gas around the detection electrode 51 due to Pt. Thus, a higher degree of concentration results in a more improved derivation accuracy of the combustible-gas concentration in the system 20 for measuring combustible-gas concentration.

Specifically, the degree of concentration is preferably 0.1 or more, more preferably 0.3 or more. The upper limit of the degree of concentration is not particularly set. For example, the detection electrode 51 may not contain Pt. The entire detection electrode 51 may be composed of Au.

The auxiliary electrode 52 is a porous electrode arranged on the upper surface of the solid electrolyte layer 44, similarly to the detection electrode 51. The auxiliary electrode 52, the solid electrolyte layer 44, and the reference electrode 53 form an electrochemical concentration cell 56. In the concentration cell 56, an electromotive force difference V, which is a potential difference depending on the difference in oxygen concentration between the auxiliary electrode 52 and the reference electrode 53, is established. The value of the electromotive force difference V is used to derive the oxygen concentration (oxygen partial pressure) in the target gas. The auxiliary electrode 52 may be composed of a catalytically active noble metal. For example, Pt, Ir, Rh, Rd, or an alloy containing at least one thereof can be used for the auxiliary electrode 52. In this embodiment, the auxiliary electrode 52 is composed of Pt.

The reference electrode 53 is a porous electrode arranged on the lower surface of the solid electrolyte layer 44, i.e., arranged on a side of the solid electrolyte layer 44 opposite that on which the detection electrode 51 and the auxiliary electrode 52 are arranged. The reference electrode 53 is exposed in the reference gas introduction cavity 46, and a reference gas (here, air) in the reference gas introduction cavity 46 is introduced thereinto. The potential of the reference electrode 53 is the standard for the electromotive force EMF and the electromotive force difference V. The reference electrode 53 may be composed of a catalytically active noble metal. For example, Pt, Ir, Rh, Rd, or an alloy containing at least one thereof can be used for the reference electrode 53. In this embodiment, the reference electrode 53 is composed of Pt.

The porous protective layer 48 covers a surface of the sensor element 31 including the detection electrode 51 and the auxiliary electrode 52. For example, the porous protective layer 48 serves to inhibit the occurrence of cracking in the sensor element 31 due to the adhesion of water in the target gas. The porous protective layer 48 is composed of, for example, any of alumina, zirconia, spinel, cordierite, titania, or magnesia as a main component. In this embodiment, the porous protective layer 48 is composed of alumina. The thickness of the porous protective layer 48 is, but not particularly limited to, for example, 20 to 1,000 μm. The porosity of the porous protective layer 48 is, but not particularly limited to, for example, 5% by volume to 60% by volume. The porous protective layer 48 preferably has a porosity of 28% or more by volume. A porosity of 28% or more by volume results in the suppression of the fact that a hydrocarbon gas having a large number of carbon atoms fails to reach the periphery of the detection electrode 51 and the inhibition of a decrease in the measurement accuracy of the combustible-gas concentration. The sensor element 31 may not include the porous protective layer 48.

The heater portion 60 serves to control the temperature of the base 40 (in particular, the solid electrolyte layer 44) by heating and keeping it warm in order to activate the solid electrolyte of the base 40 to increase the oxygen-ion conductivity. The heater portion 60 includes a heater electrode 61, a heater 62, a through-hole 63, a heater insulating layer 64, and a lead wire 66. The heater electrode 61 is an electrode arranged so as to be in contact with a lower surface of the first substrate layer 41. The heater electrode 61 is connected to a heater power supply 77 of the apparatus 70 for measuring combustible gas concentration.

The heater 62 is an electrical resistor arranged so as to be held between the first substrate layer 41 and the second substrate layer 42. The heater 62 is connected to the heater electrode 61 through the lead wire 66 and the through-hole 63. The heater 62 is fed from the heater power supply 77 through the heater electrode 61 to generate heat, so that the base 40 included in the sensor element 31 is heated and kept warm. The heater 62 is configured to be able to control the output with a temperature sensor (here, temperature acquisition section 78) in such a manner that the mixed potential cell 55 and the concentration cell 56 (in particular, the solid electrolyte layer 44) have a predetermined operating temperature. The operating temperature is preferably 450° C. or higher because the solid electrolyte layer 44 of the mixed potential cell 55 can be appropriately activated. The operating temperature may be 600° C. or lower. The heater insulating layer 64 is an insulating layer that is arranged on upper and lower surfaces of the heater 62 and that is composed of an insulating material such as alumina, specifically porous alumina.

The apparatus 70 for measuring combustible-gas concentration is an apparatus for measuring the combustible-gas concentration in the target gas with the sensor element 31. The apparatus 70 for measuring combustible-gas concentration also serves as a controller of the sensor element 31. The apparatus 70 for measuring combustible-gas concentration includes a control section 72, an electromotive force acquisition section 75, an oxygen concentration acquisition section 76, the heater power supply 77, and the temperature acquisition section 78.

The control section 72 controls the entire apparatus and, for example, is a microprocessor including CPU, RAM, and so forth. The control section 72 includes a memory part 73 that stores a processing program and various data sets. The electromotive force acquisition section 75 is a module that acquires information about the electromotive force EMF of the mixed potential cell 55. In this embodiment, the electromotive force acquisition section 75 is connected to the detection electrode 51 and the reference electrode 53 of the mixed potential cell 55 and thus functions as a voltage detection circuit that measures an electromotive force EMF. The oxygen concentration acquisition section 76 is a module that acquires information about the oxygen concentration in the target gas. In this embodiment, the oxygen concentration acquisition section 76 is connected to the auxiliary electrode 52 and the reference electrode 53 of the concentration cell 56 and thus functions as a voltage detection circuit that measures the electromotive force difference V serving as information about the oxygen concentration. The electromotive force acquisition section 75 and the oxygen concentration acquisition section 76 output the electromotive force EMF and the electromotive force difference V that have been measured by them to the control section 72. The control section 72 derives the combustible-gas concentration which is a carbon equivalent concentration of the combustible-gas in the target gas from the electromotive force EMF and the electromotive force difference V. The heater power supply 77 is a power supply that supplies power to the heater 62, and the output power is controlled by the control section 72. The temperature acquisition section 78 is a module that acquires a value about the temperature of the heater 62 (here, value of resistance). The temperature acquisition section 78 acquires the value of resistance of the heater 62 by, for example, connecting the temperature acquisition section 78 to the heater electrode 61, allowing a minute electric current to flow, and measuring a voltage.

Each of the detection electrode 51, the auxiliary electrode 52, and the reference electrode 53 is electrically connected to a corresponding one of lead wires arranged toward the other end of the sensor element 31 (right side of FIG. 2) (not illustrated in FIG. 2). The electromotive force acquisition section 75 and the oxygen concentration acquisition section 76 measure the electromotive force EMF and the electromotive force difference V, respectively, through the lead wires.

Figure 3:
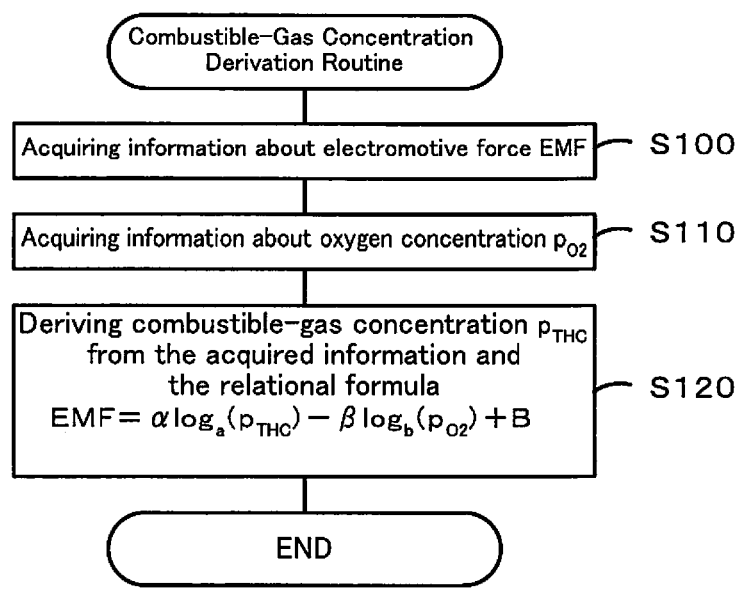
FIG. 3 is a flow chart illustrating an example of a combustible-gas concentration derivation routine.

The measurement of the combustible-gas concentration with the system 20 for measuring combustible-gas concentration will be described below. FIG. 3 is a flow chart illustrating an example of an combustible-gas concentration derivation routine executed by the control section 72. The routine is stored in, for example, the memory part 73 of the control section 72. When a command to derive combustible-gas concentration is fed from the engine ECU 9, the routine is repeatedly executed, for example, with a predetermined period (for example, several milliseconds to several tens of milliseconds). The control section 72 controls, in advance, the temperature of the mixed potential cell 55 and the concentration cell 56 to a predetermined operating temperature (for example, a temperature in the range of 450° C. or higher and 650° C. or lower) by controlling the output power of the heater power supply 77 to produce heat from the heater 62. For example, the control section 72 controls the temperature of the mixed potential cell 55 and the concentration cell 56 to a predetermined operating temperature by controlling the output power of the heater power supply 77 in such a manner that the temperature (here, resistance) of the heater 62 acquired by the temperature acquisition section 78 is a predetermined value.

When the combustible-gas concentration derivation routine is started, the control section 72 executes an electromotive force acquisition step of acquiring information about the electromotive force EMF of the mixed potential cell 55 with the electromotive force acquisition section 75 (step S100). In this embodiment, the control section 72 acquires the value of the electromotive force EMF measured by the electromotive force acquisition section 75 on an as-is basis. The control section 72 executes the combustible-gas concentration derivation routine in a state in which, basically, an exhaust gas from the engine 1 flows through the pipe 10 and the protective cover 32. Thus, the control section 72 acquires the electromotive force EMF of the mixed potential cell 55 while the detection electrode 51 is exposed to the target gas. Here, in the mixed potential cell 55, electrochemical reactions, such as the oxidation of combustible-gas (particularly, hydrocarbon gas) and the ionization of oxygen in the target gas, occur at the triple phase boundary of the detection electrode 51, the solid electrolyte layer 44 and the target gas to establish a mixed potential on the detection electrode 51. Thus, the electromotive force EMF is a value based on the combustible-gas concentration and the oxygen concentration in the target gas.

The control section 72 executes an oxygen concentration acquisition step of acquiring information about oxygen concentration in the target gas with the oxygen concentration acquisition section 76 (step S110). In this embodiment, the control section 72 acquires the electromotive force difference V of the concentration cell 56 from the oxygen concentration acquisition section 76. Here, in the concentration cell 56, the electromotive force difference V is generated between the auxiliary electrode 52 and the reference electrode 53, depending on the difference in oxygen concentration between the target gas and air in the reference gas introduction cavity 46. Hydrocarbons, $NH_3$, CO, NO, $NO_2$ in the target gas are subjected to redox by the catalysis of Pt serving as the auxiliary electrode 52. The concentrations of these gas components in the target gas are significantly lower than the oxygen concentration in the target gas. Thus, the occurrence of the redox has little influence on the oxygen concentration in the target gas. Accordingly, the electromotive force difference V is a value based on the oxygen concentration in the target gas. By the control section 72, any one of step S100 and step S110 may be first executed, or the steps may be executed in parallel.

Subsequently, the control section 72 executes a concentration derivation step (step S120) of deriving the combustible-gas concentration serving as the carbon-equivalent concentration of the combustible gas in the target gas from the information about the electromotive force EMF acquired in step S100, the information about the oxygen concentration acquired in step S110, and the relationship represented by formula (1) and terminates the routine. The relationship represented by formula (1) is stored in, for example, the memory part 73, in advance.

$$EMF = \alpha \log_a(p_{THC}) - \beta \log_b(p_{O2}) + B \quad (1)$$

(where
EMF: the electromotive force of the mixed potential cell,
α, β, and B: constants,
a and b: any base (provided that a≠1, a>0, b≠1, and b>0),
$p_{THC}$: the combustible-gas concentration in the target gas, and
$p_{O2}$: the oxygen concentration in the target gas).

In step S120, the control section 72 replaces "EMF" in formula (1) by the value of the electromotive force EMF acquired in step S100. The control section 72 derives the oxygen concentration $p_{O2}$ from the electromotive force difference V acquired in step S110 and the relationship, which is stored in the memory part 73 in advance, between the electromotive force difference V and the oxygen concentration $p_{O2}$ and replaces "$p_{O2}$" in formula (1) by the derived value. The control section 72 derives the combustible-gas concentration $p_{THC}$ in formula (1). The units of the electromotive force EMF may be, for example, [mV]. The combustible-gas concentration $p_{THC}$ is a value (carbon-equivalent value) obtained by multiplying the volume fraction of the combustible gas in the target gas by the number of carbon atoms. For example, the combustible-gas concentration $p_{THC}$ may be a value given in parts per million [ppmC], a value given in percent [% C], or a dimensionless value (for example, in the case of 10% C, a value of 0.1). The oxygen concentration $p_{O2}$ represents the volume fraction of oxygen in the target gas. The oxygen concentration $p_{O2}$ may be a value given in, for example, parts per million [ppm], a value given in percent [%], or a dimensionless value (for example, in the case of 10%, a value of 0.1). $p_{THC}$ and $p_{O2}$ may be given in different units. Each of the bases a and b may be a value of 10 or Napier's constant e. Each of the constants α, β, and B has a value determined depending on the sensor element 31 and can have different values, depending on the sensor element 31. The constants α, β, and B can be determined by, for example, experiments described below, in advance. Each of the constants α and β may have a positive value. The derivation of the combustible-gas concentration $p_{THC}$ executed by the control section 72 on the basis of the relationship of formula (1) may be executed using the relationship of formula (1) and is not limited to the derivation of the combustible-gas concentration using formula (1) itself. For example, formula (1) itself may be stored in the memory part 73. Formula (1)' obtained by modifying the formula (1) in such a manner that the left side is "$p_{THC}$" alone may be stored. The relationship of values of the variables (EMF, $p_{THC}$, and $p_{O2}$) of formula (1) is stored as a map in the memory part 73. The control section 72 may derive the combustible-gas concentration $p_{THC}$ from the map.

[Math. 2]

$$p_{THC} = a^{EMF/\alpha + \beta/\alpha \, \log_b(pO2) - B/\alpha} \quad (1)'$$

As described above, the control section 72 derives the combustible-gas concentration $p_{THC}$ in the target gas from the relationship of formula (1) in this embodiment. Thus, the combustible-gas concentration in the target gas can be derived with higher accuracy than that in the case of using formula (2) described above. This will be described below.

As described above, formula (2) is conceived as the characteristics of the electromotive force EMF of the mixed potential-type combustible-gas sensor. However, the inventors have conducted studies and have found that in an actual sensor element (for example, the sensor element 31), the relationship among the electromotive force EMF, the combustible-gas concentration $p_{THC}$, the oxygen concentration $p_{O2}$, the $H_2O$ concentration $p_{H2O}$, and the $CO_2$ concentration $p_{CO2}$ does not obey formula (2). For example, according to formula (2), although the effect of the $H_2O$ concentration $p_{H2O}$ on the electromotive force EMF ($H_2O$ interference) and the effect of the $CO_2$ concentration $p_{CO2}$ on the electromotive force EMF ($CO_2$ interference) should be present, in fact, even if the $H_2O$ concentration $p_{H2O}$ and the $CO_2$ concentration $p_{CO2}$ were changed, the electromotive force EMF remained substantially unchanged.

With regard to the oxidation of hydrocarbon gas and the ionization of oxygen in the target gas, an anodic reaction represented by equation (a) described below and a cathodic reaction represented by equation (b) described below occur at the triple phase boundary of the mixed potential cell 55. In equation (a), "HC" represents a hydrocarbon. The coefficients a, b, and c and the number of electrons n have different values depending on the specific kind of "HC". Equation (b) is the same reaction regardless of the kind of hydrocarbon. When different hydrocarbons are present in the target gas, the number of electrons n in formula (2) described above corresponds to the sum of the numbers of electrons n's (n1, n2, ... ) in equation (a) for the kind of hydrocarbons, the electrons n's having weights corresponding to the concentrations (proportions) of the kind of hydrocarbons.

[Math. 3]

[Anodic reaction]

$$HC + aO^{2-} \rightarrow bH_2O + cCO_2 + ne^- \qquad (a)$$

[Cathodic reaction]

$$\frac{1}{2}O_2 + 2e^- \rightarrow O^{2-} \qquad (b)$$

The anodic reaction and the cathodic reaction occur simultaneously at the triple phase boundary of one detection electrode (for example, the detection electrode 51) to form a local cell, thereby establishing an electromotive force EMF. This is a mixed potential cell (for example, the mixed potential cell 55). The electromotive force EMF at this time should theoretically obey formula (2).

For actual sensor elements, however, it was found in experiments that the relationship among the variables obeys formula (1), and not formula (2). The inventors have considered that the reason for this is that $p_{THC}$, $p_{O2}$, $p_{H2O}$, and $p_{CO2}$ in formula (2) need not be replaced by the concentrations in the target gas and should be replaced by partial pressures at the triple phase boundary. Letting a combustible gas partial pressure, an $O_2$ partial pressure, a $H_2O$ partial pressure, and a $CO_2$ partial pressure at the triple phase boundary on the detection electrode be $p_{THC}^*$, $p_{O2}^*$, $p_{H2O}^*$, and $p_{CO2}^*$, respectively, formula (A1) holds. This can also be derived from formula (2). The actual electromotive force EMF seemingly obeys formula (A1), and not formula (2). $p_{THC}^*$, $p_{O2}^*$, $p_{H2O}^*$, and $p_{CO2}^*$ at the triple phase boundary cannot be directly detected; thus, a formula including $p_{THC}$, $p_{O2}$, $p_{H2O}$, and $p_{CO2}$ in the target gas needs to be derived from formula (A1). The inventors thought that we could explain below that formula (1) including $p_{THC}$, $p_{O2}$, $p_{H2O}$, and $p_{CO2}$ holds on the basis of formula (A1).

[Math. 4]

$$EMF = \frac{RT}{nF}(K1 \ln p_{THC}^* - K2 \ln p_{O2}^* - K3 \ln p_{H2O}^* - K4 \ln p_{CO2}^*) + K5 \qquad (A1)$$

Let us first consider a mixed potential equation from a microscopic point of view. As described above, the partial pressures, $\ln p_{THC}^*$, $\ln p_{O2}^*$, $\ln p_{H2O}^*$, and $\ln p_{CO2}^*$, at the triple phase boundary on the detection electrode are not equal to the partial pressures, $\ln p_{THC}$, $\ln p_{O2}$, $\ln p_{H2O}$, and $\ln p_{CO2}$, in an ambient gas (target gas). This is because the following dynamic changes occur in the electrochemical reactions: molecules in a gas phase are adsorbed onto a surface of the detection electrode, diffused on the surface of the detection electrode to reach the triple phase boundary, and subjected to electrochemical reactions, and the resulting products are desorbed from the surface of the detection electrode, rather than the fact that the molecules directly reach the triple phase boundary from the gas phase. Let us now consider the product $H_2O$ and $CO_2$ formed in the anodic reaction. The formed $H_2O$ and $CO_2$ are seemingly adsorbed on the detection electrode and then desorbed into the gas phase. Because large amounts of $H_2O$ and $CO_2$ are present in the target gas, the $H_2O$ and $CO_2$ formed in the anodic reaction seem to be not readily desorbed from the surface of the detection electrode. It is thus considered that the $H_2O$ partial pressure $p_{H2O}^*$ and the $CO_2$ partial pressure $p_{CO2}^*$ at the triple phase boundary during the adsorption of $H_2O$ and $CO_2$ are larger than the $H_2O$ partial pressure $p_{H2O}$ and the $CO_2$ partial pressure $p_{CO2}$ in the target gas and that formula (A2) described below always holds. In the target gas (here, an exhaust gas), the $H_2O$ concentration and the $CO_2$ concentration are usually about 5% to about 15%, and the total pressure remains constant at 1 atm. For the sake of safety, considering that the $H_2O$ concentration and the $CO_2$ concentration vary in a wide range of 1% to 20%, formula (A3) described below holds.

$$p_{H2O}^* > p_{H2O}, p_{CO2}^* > p_{CO2} \qquad (A2)$$

$$0.01 \text{ atm} < p_{H2O} < 0.2 \text{ atm}, 0.01 \text{ atm} < p_{CO2} < 0.2 \text{ atm} \qquad (A3)$$

Let us next consider that what will become of $p_{H2O}^*$ when $p_{H2O}$ is changed while $H_2O$ is adsorbed on the surface of the detection electrode. With regard to $H_2O$ at the triple phase boundary, $H_2O$ adsorbed on the detection electrode is denoted by $H_2O(ad)$, and $H_2O$ in the gas phase is denoted by $H_2O$ (gas). The partial pressure of $H_2O$ adsorbed on the detection electrode is denoted by $p_{H2O(ad)}$, and the partial pressure of $H_2O$ in the gas phase is denoted by $p_{H2O(gas)}$. Thus, $p_{H2O}^* = p_{H2O(ad)} + p_{H2O(gas)}$. $p_{H2O(ad)}$ includes the partial pressure of $H_2O$ that comes from the target gas and that is adsorbed on the detection electrode, and the partial pressure of $H_2O$ that is formed by the anodic reaction (the foregoing equation (a)) and that is adsorbed on the detection electrode. $p_{H2O(gas)}$ includes the partial pressure of $H_2O$ that is contained in the target gas and that is present at the triple phase boundary in a gas phase state, and the partial pressure of $H_2O$ that is formed by the anodic reaction and that is in a gas phase state. With regard to $H_2O(ad)$ and $H_2O(gas)$, formulae (A4) and (A5) described below hold, provided that an equilibrium constant $K_{H2O}$=(constant). Although $p_{H2O}^*$ is supposed to be changed according to formulae (A4) and (A5), in fact, it behaves differently. The reason for this is presumably that $p_{H2O}$ changes in the range represented by formula (A3) described above, whereas $p_{H2O(ad)}$ cannot change once the adsorption of $H_2O$ on the detection electrode is stabilized and reaches a steady state (=1 atm). The reason $p_{H2O(ad)}$ is 1 atm in the steady state is described below. Because $H_2O_{(ad)}$ adsorbed on the detection electrode is not in the gas phase, the amount of $H_2O(ad)$ is expressed as activity $a_{H2O(ad)}$, and not as partial pressure, to be exact. When $H_2O(ad)$ is regarded as a solid, the activity $a_{H2O(ad)}$ have a value of 1 (i.e., the activity is 1 irrespective of the amount adsorbed), and an activity of 1 can be regarded as comparable to a partial pressure of 1 atm.

[Math. 5]

$$H_2O(ad) \overset{K_{H2O}}{\rightleftharpoons} H_2O(gas) \qquad (A4')$$

$$K_{H2O} = \frac{p_{H2O(ad)}}{p_{H2O(gas)}} = \frac{p_{H2O}^* - p_{H2O(gas)}}{p_{H2O(gas)}} \qquad (A5')$$

Accordingly, $p_{H2O(ad)}$ can be regarded as 1 atm. Although as with formula (A3), $p_{H2O(gas)}$ seems to be about 0.01 to about 0.2 atm, because $H_2O(ad)$, which can be regarded as 1 atm, is present on the surface of the detection electrode, $H_2O$ in the gas phase is less likely to contribute to the reaction, the partial pressure $p_{H2O(gas)}$ of $H_2O$ present in the gas phase at the triple phase boundary seems to have a value significantly smaller than 0.01 to 0.2 atm. Thus, $p_{H2O(ad)} \gg p_{H2O(gas)}$ seemingly holds, and $p_{H2O(gas)}$ seems to have a very small, negligible value. Accordingly, even if $p_{H2O}$ changes while $H_2O$ is adsorbed on the surface of the detection electrode, $p_{H2O}^*$ can be regarded as constant, as represented by formula (A6). Thus, formula (A1) can be regarded as formula (A7). That is, the $H_2O$ partial pressure $p_{H2O}^*$ at the triple phase boundary can be regarded as having no effect ($H_2O$ interference) on the electromotive force EMF. The constant K6 in formula (A7) is the sum of the term in $p_{H2O}^*$ (=constant) in formula (A1) and the constant K5.

[Math. 6]

$$p_{H2O}^* = p_{H2O(ad)} + p_{H2O(gas)} \fallingdotseq p_{H2O(ad)} = \text{constant}(1 \text{ atm}) \qquad (A6)$$

$$EMF = \frac{RT}{nF}(K1 \ln p_{THC}^* - K2\ln p_{O2}^* - K4 \ln p_{CO2}^*) + K6 \qquad (A7)$$

Let us next consider that, as with $H_2O$, what will become of $p_{CO2}^*$ when $p_{CO2}$ is changed while $CO_2$ is adsorbed on the surface of the detection electrode. With regard to $CO_2$ at the triple phase boundary, $CO_2$ adsorbed on the detection electrode is denoted by $CO_2(ad)$, and $CO_2$ in the gas phase is denoted by $CO_2(gas)$. The partial pressure of $CO_2$ adsorbed on the detection electrode is denoted by $p_{CO2}(ad)$, and the partial pressure of $CO_2$ in the gas phase is denoted by $p_{CO2}(gas)$. Thus $p_{CO2}^* = p_{CO2}(ad) + p_{CO2}(gas)$. $p_{CO2}(ad)$ includes the partial pressure of $CO_2$ that comes from the target gas and that is adsorbed on the detection electrode; and the partial pressure of $CO_2$ that is formed by the anodic reaction (equation (a)) and that is adsorbed on the detection electrode. $p_{CO2}(gas)$ includes the partial pressure of $CO_2$ that is contained in the target gas and that is present at the triple phase boundary in a gas phase state; and the partial pressure of $CO_2$ that is formed by the anodic reaction and that is in a gas phase state. With regard to $CO_2(ad)$ and $CO_2(gas)$, formulae (A4') and (A5') described below hold, provided that an equilibrium constant $K_{CO2}$=(constant). Although $p_{CO2}^*$ is supposed to be changed according to formulae (A4') and (A5'), in fact, it behaves differently. The reason for this is presumably that $p_{CO2}$ changes in the range represented by formula (A3) described above, whereas $p_{CO2}(ad)$ cannot change once the adsorption of $CO_2$ on the detection electrode is stabilized and reaches a steady state (=1 atm). The reason $p_{CO2}(ad)$ can be regarded as 1 atm in the steady state is described below. Because $CO_2(ad)$ adsorbed on the detection electrode is not in the gas phase, the amount of $CO_2(ad)$ is expressed as activity $aCO_2(ad)$, and not as partial pressure, to be exact. When $CO_2(ad)$ is regarded as a solid, the activity $aCO_2(ad)$ has a value of 1 (i.e., the activity is 1 irrespective of the amount adsorbed on the detection electrode), and an activity of 1 can be regarded as comparable to a partial pressure of 1 atm.

[Math. 7]

$$CO_2(ad) \underset{}{\overset{K_{CO2}}{\rightleftharpoons}} CO_2(gas) \qquad (A4')$$

$$K_{CO2} = \frac{p_{CO2(ad)}}{p_{CO2(gas)}} = \frac{p_{CO2}^* - p_{CO2(gas)}}{p_{CO2(gas)}} \qquad (A5')$$

Accordingly, $p_{CO2}(ad)$ can be regarded as 1 atm. Although, as with formula (A3), $p_{CO2}(gas)$ seems to be about 0.01 to about 0.2 atm, because $CO_2(ad)$, which can be regarded as 1 atm, is present on the surface of the detection electrode, $CO_2$ in the gas phase is less likely to contribute to the reaction, the partial pressure $p_{CO2}(gas)$ of $CO_2$ present in the gas phase at the triple phase boundary seems to have a value significantly smaller than 0.01 to 0.2 atm. Thus, $p_{CO2}(ad) \gg p_{CO2}(gas)$ seemingly holds, and $p_{CO2}(gas)$ seems to have a very small, negligible value. Accordingly, even if $p_{CO2}$ changes while $CO_2$ is adsorbed on the surface of the detection electrode, $p_{CO2}^*$ can be regarded as constant, as represented by formula (A6'). Thus, formula (A7) can be regarded as formula (A7'). That is, the $CO_2$ partial pressure $p_{CO2}^*$ at the triple phase boundary can be regarded as having no effect ($CO_2$ interference) on the electromotive force EMF. The constant K7 in formula (A7') is the sum of the term in $p_{CO2}^*$ (=constant) in formula (A7) and the constant K6.

[Math. 8]

$$p_{CO2}^* = p_{CO2(ad)} + p_{CO2(gas)} \fallingdotseq p_{CO2(ad)} = \text{constant}(1 \text{ atm}) \qquad (A6')$$

$$EMF = \frac{RT}{nF}(K1 \ln p_{THC}^* - K2\ln p_{O2}^*) + K7 \qquad (A7')$$

Let us then consider a mixed potential equation from a macroscopic point of view. When the total pressure of the target gas is 1 atm, the concentration is equal to the partial pressure; thus, $p_{THC}$, $p_{O2}$, $p_{H2O}$, and $p_{CO2}$ will be explained below as partial pressures. Formula (A8) can be derived from formula (A3). Formula (A9) can be derived from formulae (A6) and (A6'). From formulae (A8) and (A9), formula (A10) holds. Letting the ratio of $\ln p_{H2O}^*$ to $\ln p_{H2O}$ be a pressure adjustment factor $\delta$ and letting the ratio of $\ln p_{CO2}^*$ to $\ln p_{CO2}$ be a pressure adjustment factor $\delta'$, $\delta$ and $\delta'$ are defined by formula (A11). From formula (A10), $\delta$ satisfies $-1<\delta<1$, and $\delta'$ satisfies $-1<\delta'<1$. Similarly, letting the ratio of $\ln p_{THC}^*$ to $\ln p_{THC}$ be a pressure adjustment factor $\delta''$, $\delta''$ is defined by formula (A12). The pressure adjustment factors $\delta$, $\delta'$, and $\delta''$ are values characteristic of the sensor element, depending on, for example, the composition and the structure of the detection electrode.

$$-4.6 < \ln p_{H2O} < -1.6, \; -4.6 < \ln p_{CO2} < -1.6 \qquad (A8)$$

$$\ln p_{H2O}^* \approx 0, \; \ln p_{CO2}^* \approx 0 \qquad (A9)$$

$$|\ln p_{H2O}^*| < |\ln p_{H2O}|, \; |\ln p_{CO2}^*| < |\ln p_{CO2}| \qquad (A10)$$

$$\delta = \ln p_{H2O}^*/\ln p_{H2O}, \; \delta' = \ln p_{CO2}^*/\ln p_{CO2} \qquad (A11)$$

$$\delta'' = \ln p_{THC}^*/\ln p_{THC} \qquad (A12)$$

Formula (A1) is transformed using the pressure adjustment factors $\delta$, $\delta'$, and $\delta''$ to derive formula (A13). Formula (A13) is obtained by substituting "$\ln p_{H2O}^* = \delta \times \ln p_{H2O}$, and $\ln p_{CO2}^* = \delta' \times \ln p_{CO2}$" obtained from formula (A11), "$\ln p_{THC}^* = \delta'' \times \ln p_{THC}$" obtained from formula (A12), and "$\ln p_{O2}^* = \ln p_{O2}$" in formula (A1). In existing $O_2$ sensors and SOFCs, it is well known that the relationship between the oxygen concentration and the electromotive force obeys the Nernst equation; hence, it is clear that $\ln p_{O2}^* = \ln p_{O2}$ holds.

[Math. 9]

$$EMF = \frac{RT}{nF}(K1\delta'' \ln p_{THC} - K2 \ln p_{O2} - K3\delta \ln p_{H2O} - K4\delta' \ln p_{CO2}) + K5 \quad (A13)$$

From formulae (A6), (A6'), and (A11), $\ln p_{H2O}^* = \delta \times \ln p_{H2O} = 0$, and $\ln p_{CO2}^* = \delta' \times \ln p_{CO2} = 0$ hold. Thus, formula (A13) can be expressed as formula (A14). The constants K1, K2, and K5 are values characteristics of the sensor element, depending on, for example, the composition and the structure of the detection electrode. In formula (A14), letting the base of the logarithm be freely selected values a and b, letting the coefficients of the terms in the right side be constants α and β, and letting the constant K5 be the constant B, formula (1) is derived.

[Math. 10]

$$EMF = \frac{RT}{nF}(K1\delta'' \ln p_{THC} - K2 \ln p_{O2}) + K5 \quad (A14)$$

Unlike formula (2), formula (1) can express the fact that the substantially no $H_2O$ interference or $CO_2$ interference is present. Thus, the use of formula (1) can derive the combustible-gas concentration $p_{THC}$ with higher accuracy than that in the case of using formula (2). Formula (1) can be used not only when the total pressure of the target gas is 1 atm, but also when the total pressure is about 1 atm (for example, 0.9 atm to 1.10 atm). Formula (1) can also be used when the total pressure of the target gas is not about 1 atm.

A method for deriving the constants α, β, and B in formula (1) will be described below. The constants α, β, and B may be derived by a method for deriving a constant, the method including (a) a step of multiple times of executing electromotive force measurement processing that measures an electromotive force EMF of the mixed potential cell 55 in a state in which the detection electrode 51 is exposed to the target gas while at least one of oxygen concentration and the carbon-equivalent concentration of at least one combustible gas of one or more combustible gases in the target gas is changed, a gas containing oxygen and the one or more combustible gases being used as the target gas; and (b) a step of deriving constants α, β, and B in formula (1) from results of the electromotive force measurement processing executed multiple times.

Figure 4:
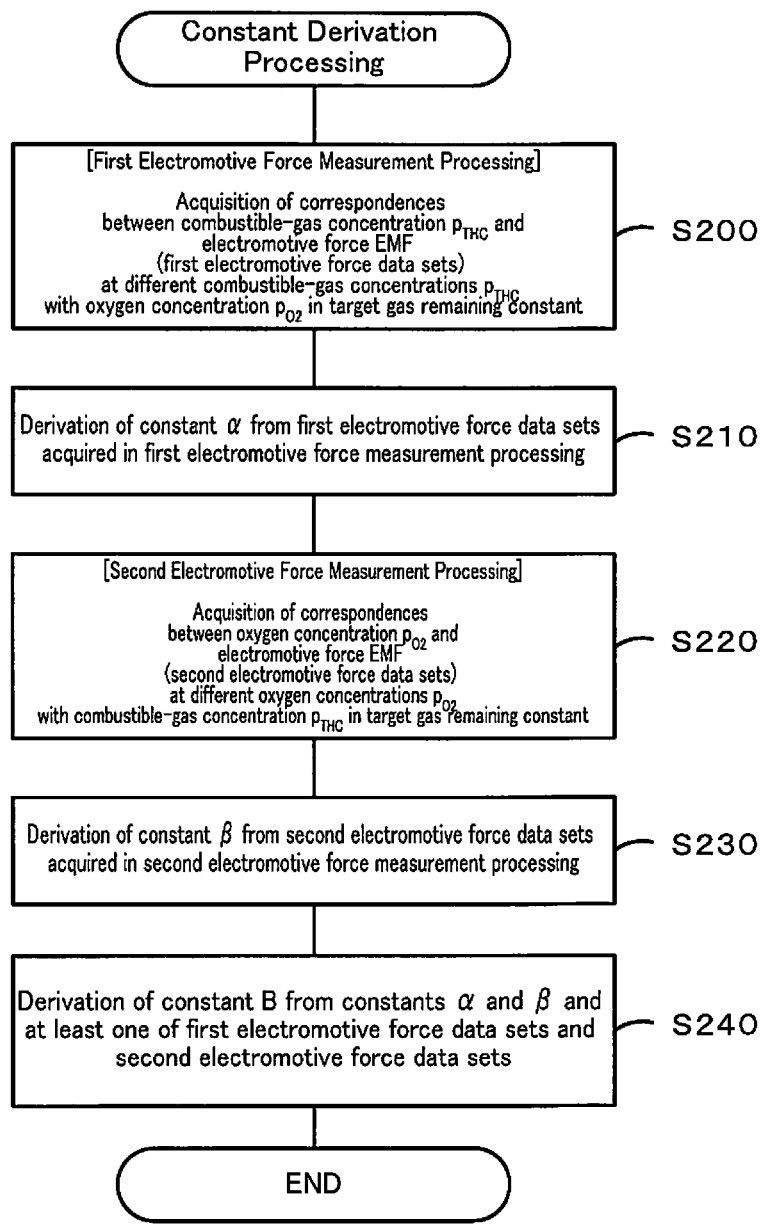
FIG. 4 is a flow chart illustrating an example of constant derivation processing.

For example, the method for deriving a constant may be executed as described below. FIG. 4 is a flow chart illustrating an example of constant derivation processing. In this constant derivation processing, processing including substeps (a1) and (a2) is executed as step (a), and processing including substeps (b1) to (b3) is executed as step (b). In the constant derivation processing, the sensor element 31, which is a target with the constants to be derived, is subjected to, as substep (a1), first electromotive force measurement processing for acquiring first electromotive force data multiple times, the first electromotive force data expressing the correspondence between the combustible-gas concentration $p_{THC}$ and the electromotive force EMF (substep S200).

Specifically, the correspondence between the combustible-gas concentration $p_{THC}$ and the electromotive force EMF is acquired as the first electromotive force data by exposing the sensor element 31 to the target gas with the oxygen concentration $p_{O2}$ and the combustible-gas concentration $p_{THC}$ that have been adjusted to predetermined values and measuring the electromotive force EMF. Next, first electromotive force data sets are similarly acquired by measuring the electromotive force EMF multiple times at different combustible-gas concentrations $p_{THC}$ in the target gas while the oxygen concentration $p_{O2}$ in the target gas remains unchanged (constant). After the first electromotive force data sets are acquired by executing substep (a1) as described above, processing for deriving the constant α from the acquired data sets is executed as substep (b1) (substep S210). Specifically, the slope obtained when the relationship between the logarithm of the combustible-gas concentration $p_{THC}$, $\log_a(p_{THC})$, in the first electromotive force data sets acquired by executing the first electromotive force measurement processing multiple times and the electromotive force EMF is approximated by a straight line (linear function) is derived as the constant α. The approximation is performed on the basis of, for example, the method of least squares. As described above, the multiple execution of the first electromotive force measurement processing at a constant oxygen concentration in substep (a1) facilitates the derivation of the constant α in substep (b1).

Next, the sensor element 31, which is a target with the constants to be derived, is subjected to, as substep (a2), second electromotive force measurement processing for acquiring second electromotive force data multiple times, the second electromotive force data expressing the correspondence between the oxygen concentration $p_{O2}$ and the electromotive force EMF (substep S220). The second electromotive force measurement processing executed multiple times can be executed in the same way as in substep (a1), except that different oxygen concentrations $p_{O2}$ are used while the combustible-gas concentration $p_{THC}$ in the target gas remains constant. Processing for deriving the constant β from the second electromotive force data sets acquired by the second electromotive force measurement processing executed multiple times is then executed as substep (b2) (substep S230). In this processing, as with the processing in substep S210, the slope obtained when the relationship between the logarithm of the oxygen concentration $p_{O2}$, $\log_b(p_{O2})$, and the electromotive force EMF is approximated by a straight line (linear function) is derived as the constant β. As described above, the multiple execution of the second electromotive force measurement processing at a constant combustible-gas concentration in substep (a2) facilitates the derivation of the constant β in substep (b2).

Processing for deriving the constant B from the constants α and β derived in substeps (b1) and (b2) and the results of electromotive force measurement processing one or more times in at least one of substeps (a1) and (a2) is then executed as substep (b3) (substep S240). For example, in substep (b3), the constant B may be derived by substituting the derived constants α and β, the logarithm of the combustible-gas concentration $p_{THC}$, $\log_a(p_{THC})$, the logarithm of the constant oxygen concentration $p_{O2}$, $\log_b(p_{O2})$, and the electromotive force EMF in the first electromotive force data sets in formula (1). At this time, the average of the constants B derived from each of the first electromotive force data sets may be defined as the constant B in formula (1). Similarly, the constant B may be derived from the one or more second electromotive force data sets. The average of the constants B derived from the first electromotive force data sets and the constants B derived from the second electromotive force data sets may be defined as the constant B in formula (1). Substep (S240) is executed to terminate the constant derivation processing.

The first electromotive force data sets and the second electromotive force data sets are measured in a state in which the mixed potential cell 55 is heated with the heater 62 to a predetermined fixed operating temperature. Comparisons between formula (1) and formula (A14) reveal that the constants α and β vary depending on the temperature T of the mixed potential cell 55, i.e., the operating temperature of the sensor element 31 in use. Thus, in the case where one sensor element 31 can be used at different operating temperatures, the constants α and β in formula (1) are derived at each of the different operating temperatures and stored in, for example, the memory part 73, in advance. When the control section 72 executes the combustible gas concentration derivation processing, the constants α and β corresponding to the operating temperature of the sensor element 31 are used. The constant B can also vary depending on the operating temperature of the sensor element 31 in use; thus, the constant B may be derived at each of the different operating temperatures and stored in, for example, the memory part 73, in advance.

In the case of executing the electromotive force measurement processing for deriving the constants α, β, and B in step (a), the question now arises as to what kind of combustible gas is specifically used as the combustible gas in the target gas. More specifically, a question arises as to what kind of hydrocarbon gas is used as the combustible gas in the target gas. In this respect, for example, it is conceived that an exhaust gas of an actual engine is used as the target gas for the electromotive force measurement processing. However, the kinds and proportions of hydrocarbon gases in the exhaust gases of different engines are different, and the kind of engine for which the sensor element is used is uncertain in advance, in some cases. In the case of performing substeps (a1) and (a2), another question is the fact that it is difficult to fixing one of the combustible-gas concentration $p_{THC}$ in the exhaust gas of an actual engine and the oxygen concentration $p_{O2}$ while the other is changed. For example, if a fuel is injected into the engine in such a manner that the air-fuel ratio is leaner in order to achieve a higher oxygen concentration $p_{O2}$ in the exhaust gas, hydrocarbons in the exhaust gas can be reduced to reduce the combustible-gas concentration $p_{THC}$. Similarly, if the fuel is injected into the engine in such a manner that the air-fuel ratio is richer in order to achieve a lower oxygen concentration $p_{O2}$ in the exhaust gas, hydrocarbons in the exhaust gas can be increased to increase the combustible-gas concentration $p_{THC}$.

In this regard, the inventors have found that in an exhaust gas of an engine, proportions of hydrocarbons having 3 or more carbon atoms and having a higher molecular weight are higher than the proportions of hydrocarbons having 2 or less carbon atoms in terms of carbon-equivalent concentration. The inventors have also found that the degrees of effect (sensitivity) of hydrocarbons, excluding alkanes, having 3 or more carbon atoms on the electromotive force EMF of a mixed potential cell are higher than those of hydrocarbons having 2 or less carbon atoms. Thus, in step (a), preferably, letting one or more kinds of hydrocarbons among hydrocarbons, excluding alkanes, having 3 or more carbon atoms be a particular hydrocarbon, the electromotive force measurement processing is executed using a gas containing oxygen and the particular hydrocarbon as a target gas. In this case, in step (b), the constants α, β, and B are preferably derived by regarding the carbon-equivalent concentration of the particular hydrocarbon as the combustible-gas concentration $p_{THC}$. As described above, when the hydrocarbons, excluding alkanes, having 3 or more carbon atoms are used, the hydrocarbons being contained in exhaust gases of engines in larger amounts and having high degrees of effect (sensitivity) on the electromotive force EMF of a mixed potential cell, more appropriate constants α, β, and B can be derived. Here, when the electromotive force measurement processing is executed multiple times in step (a), at least one of the oxygen concentration and the carbon-equivalent concentration of the particular hydrocarbon in the target gas may be changed. In this case, one or more kinds of hydrocarbons that have 3 or more carbon atoms, that have a double bond, and that do not have a triple bond, (hereinafter, referred to as "alkenes having 3 or more carbon atoms and so forth") may be defined as the particular hydrocarbon. The alkenes having 3 or more carbon atoms and so forth include hydrocarbons that have 3 or more carbon atoms, that have two or more double bonds, and that do not have a triple bond (for example, $C_4H_6$:butadiene) in addition to alkenes having 3 or more carbon atoms. One or more alkenes among alkenes having 3 or more carbon atoms may be used as the particular hydrocarbon.

The target gas used in step (a) may not contain a hydrocarbon gas other than the particular hydrocarbon. For example, in the case where one or more kinds of hydrocarbons, excluding alkanes, having 3 or more carbon atoms are used as the particular hydrocarbon, the hydrocarbon in the target gas may be one or more kinds of hydrocarbons only among hydrocarbons, excluding alkanes, having 3 or more carbon atoms in step (a). Similarly, in the case where one or more alkenes having 3 or more carbon atoms are used as the particular hydrocarbon, the hydrocarbon in the target gas may be one or more alkenes only among alkenes having 3 or more carbon atoms in step (a). In step (a), the target gas may contain a single kind of hydrocarbon. In this case, because the target gas used in step (a) is easily prepared, the constants α, β, and B can be more easily derived.

In the case where substeps (a1), (a2), and (b1) to (b3) are performed, in substep (a1), the electromotive force measurement processing may be executed multiple times at a constant oxygen concentration and different carbon-equivalent concentrations of the particular hydrocarbon in the target gas. Similarly, in substep (a2), the electromotive force measurement processing may be executed multiple times at a constant carbon-equivalent concentration of the particular hydrocarbon and different oxygen concentrations in the target gas. In substeps (b1) to (b3), the constants may be derived by regarding the carbon-equivalent concentration of the particular hydrocarbon as the combustible-gas concentration $p_{THC}$. The "particular hydrocarbon" in substeps (a1) and (b1) may be the same as the "particular hydrocarbon" in substeps (a2) and (b2). Alternatively, at least one hydrocarbon may be different.

The reasons the degrees of effect (sensitivity) of hydrocarbons, excluding alkanes, having 3 or more carbon atoms on the electromotive force EMF of the mixed potential cell are higher than those of hydrocarbons having 2 or less carbon atoms are presumably as follows: With regard to a mixed potential reaction, hydrocarbons having a larger number of carbon atoms tend to have a lower reaction resistance of the anodic reaction (equation (a)). With regard to the mixed potential reaction, hydrocarbons having a larger number of unstable bonds between carbon atoms have a lower reaction resistance of the anodic reaction (equation (a)). For example, comparisons among hydrocarbons having the same number of carbon atoms indicate that the reaction resistance is in the following order: alkanes>alkenes>alkynes. Accordingly, it seems that hydrocarbons having a large number of carbon atoms and excluding alkanes have a low reaction resistance of the anodic reaction and have high degrees of effect (sensitivity) on the electromotive force EMF of the mixed potential cell.

Because hydrocarbons having a larger number of unstable bonds between carbon atoms seemingly have a higher sensitivity to the electromotive force EMF as described above, the sensitivity of hydrocarbons having a triple bond, such as alkynes, to the electromotive force EMF seemingly tends to be higher than that of hydrocarbons that have a double bond and that do not have a triple bond, such as alkenes. However, proportions of hydrocarbons having 3 or more carbon atoms and a triple bond in the all hydrocarbons in the exhaust gas of an engine are often very low. Thus, the constants are preferably derived using a target gas containing a hydrocarbon that has 3 or more carbon atoms, that has a double bond, and that does not have a triple bond, rather than the derivation of the constants using a target gas containing a hydrocarbon having 3 or more carbon atoms and having a triple bond.

The inventors have found that all the hydrocarbons that have 3 or more carbon atoms, that have a double bond, and that do not have a triple bond (for example, alkenes having 3 or more carbon atoms) have substantially the same sensitivity to the electromotive force EMF. Thus, the use of any of hydrocarbons such as alkenes having 3 or more carbon atoms can more appropriately derive the constants α, β, and B.

The reason all the hydrocarbons such as alkenes having 3 or more carbon atoms have substantially the same sensitivity to the electromotive force EMF is presumably that the same anodic reaction occurs at the triple phase boundary of any of the hydrocarbons. More specifically, for example, in the case of any of alkenes having 4 or more carbon atoms, it seems that after the occurrence of a decomposition reaction into an alkene having 3 carbon atoms ($C_3H_6$:propylene), an anodic reaction occurs. For example, in the cases of $C_4H_8$ and $C_8H_{16}$, it seems that after reactions (c) and (d) occur, the same anodic reaction (equation (e)) occurs. Each of reactions (c) and (d) exemplifies the case where an alkene having 4 or more carbon atoms is decomposed into an alkene having 3 carbon atoms. In the case of "alkenes having 4 or more carbon atoms and so forth", such as hydrocarbons each having multiple double bonds (for example, $C_3H_2$), other than alkene, it seems that when they are decomposed into an alkene having 3 carbon atoms, they receive hydrogen ions ($H^+$) from the surrounding $H_2O$ gas or $H_2O$ adsorbed on the detection electrode 51 and then are decomposed into the alkene having 3 carbon atoms.

$$3C_4H_8 \rightarrow 4C_3H_6 \tag{c}$$

$$3C_8H_{16} \rightarrow 8C_3H_6 \tag{d}$$

$$C_3H_6 \rightarrow 3H_2O + 3CO_2 + 18e^- \tag{e}$$

Figure 5:
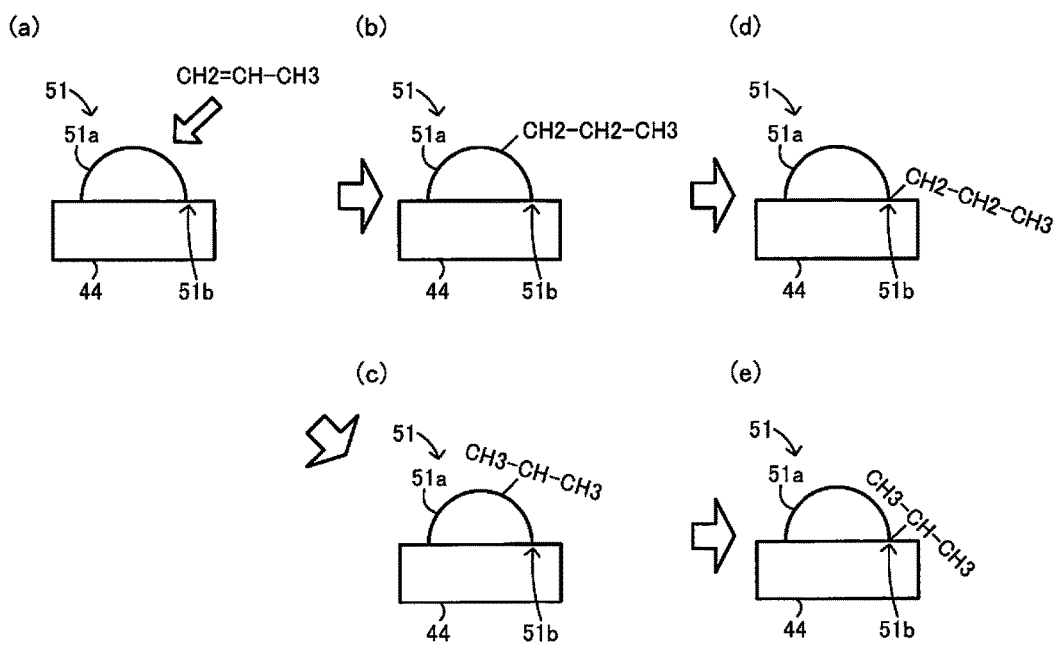
FIG. 5 is a schematic view illustrating states in which $C_3H_6$ is adsorbed on a detection electrode 51 and then moves to a triple phase boundary.

FIG. 5 is a schematic view illustrating states in which $C_3H_6$ is adsorbed on the detection electrode 51 and then moves to a triple phase boundary. In the case of $C_3H_6$ (part (a) of FIG. 5) present around a noble metal particle 51a (for example, a Au particle) on the detection electrode 51, it seems that after its double bond is cleaved, a cleaved portion is attached to (adsorbed on) the noble metal particle 51a. Thus, a terminal carbon atom of $C_3H_6$ is adsorbed on the noble metal particle 51a (part (b) of FIG. 5), or a central carbon atom thereof is adsorbed on the noble metal particle 51a (part (c) of FIG. 5). It seems that after the adsorption, $C_3H_6$ moves along the surface of the noble metal particle 51a to a triple phase boundary 51b (parts (d) and (e) of FIG. 5), the anodic reaction (equation (e)) occurs. In the case where alkenes having 4 or more carbon atoms and so forth are adsorbed on the surface of the noble metal particle 51a of the detection electrode 51, it also seems that after the alkenes are decomposed into $C_3H_6$, $C_3H_6$ is adsorbed on the detection electrode 51 and then moves to the triple phase boundary as illustrated in parts (b) and (c) of FIG. 5. That is, hydrocarbons having a long carbon chain are less likely to be adsorbed on the surface of the detection electrode 51 when their shapes are maintained; thus, it is believed that the hydrocarbons are decomposed into hydrocarbons having an appropriate number of carbon atoms and then are adsorbed on the detection electrode 51. For the reason described above, we speculate that the alkenes having 3 or more carbon atoms and so forth have substantially the same sensitivity to the electromotive force EMF.

Let us now clarify the correspondence between the constituent elements of this embodiment and constituent elements of the present invention. The solid electrolyte layer 44 of this embodiment corresponds to a solid electrolyte body of the present invention. The detection electrode 51 corresponds to a detection electrode. The reference electrode 53 corresponds to a reference electrode. The mixed potential cell 55 corresponds to a mixed potential cell. The electromotive force acquisition section 75 corresponds to an electromotive force acquisition section. The oxygen concentration acquisition section 76 corresponds to an oxygen concentration acquisition section. The control section 72 corresponds to a combustible gas concentration derivation section. In this embodiment, an example of a method for measuring a combustible-gas concentration of the present invention is also described by explaining the operation of the apparatus 70 for measuring combustible-gas concentration. Furthermore, an example of a method for deriving a constant of the present invention by explaining the method for deriving a constant of formula (1) used in the apparatus 70 for measuring combustible-gas concentration.

According to the system 2 for treating an exhaust gas described above in detail, in the apparatus 70 for measuring combustible gas concentration, the use of the relationship of formula (1) can derive the combustible gas concentration in the target gas with higher accuracy than that in the case of using formula (2) described above.

Because the detection electrode 51 is composed of the Au—Pt alloy as a main component, the mixed potential is easily established at the triple phase boundary of the solid electrolyte layer 44 and the target gas. The detection electrode 51 has a degree of concentration of 0.3 or more, which is measured by at least one of XPS and AES, and thus enables the mixed potential to be more reliably established.

The use of an operating temperature of the mixed potential cell 55 of 450° C. or higher can appropriately activate the solid electrolyte layer 44. The use of an operating temperature of the mixed potential cell 55 of 600° C. or lower can inhibit a decrease in the derivation accuracy of the combustible-gas concentration because hydrocarbons in the combustible gas are easily introduced into a reaction field around the detection electrode 51 without being oxidized.

For example, the porous protective layer 48 included in the sensor element 31 can suppress defects of the sensor element 31, such as the occurrence of cracking in the sensor element due to the adhesion of water in the target gas. The use of the porous protective layer 48 having a porosity of 28% or more by volume can inhibit a decrease in the derivation accuracy of the combustible-gas concentration.

The system 2 for treating an exhaust gas further includes one or more supply sections (here, the injector 6) arranged in the exhaust gas path 3, the one or more supply sections being configured to supply at least one of urea and ammonia, in which the engine 1 is a diesel engine, and the sensor element 31 is arranged upstream of the most upstream supply section (here, the injector 6) of the one or more supply sections arranged in the exhaust gas path 3. Here, when at least one of urea and ammonia is supplied into the exhaust gas path 3, ammonia concentration in the target gas is increased to affect the electromotive force EMF of the mixed potential cell 55 of the sensor element. In the system 2 for treating an exhaust gas according to the embodiment, the arrangement of the sensor element 31 as described above enables the combustible-gas concentration to be derived in a state in which the apparatus 70 for measuring combustible-gas concentration is affected by ammonia as little as possible. Thus, in the system 2 for treating an exhaust gas, the apparatus 70 for measuring combustible-gas concentration can derive the combustible-gas concentration with higher accuracy.

In the method for deriving a constant described above, the constants $\alpha$, $\beta$, and B are derived by performing steps (a) and (b). In substep (a1), because the electromotive force measurement processing is executed multiple times at a constant oxygen concentration, the constant $\alpha$ is easily derived in substep (b1). Similarly, because the electromotive force measurement processing is executed multiple times at a constant carbon-equivalent concentration of the particular hydrocarbon in substep (a2), the constant $\beta$ is easily derived in substep (b2). In step (b), the constants $\alpha$, $\beta$, and B are derived by regarding the carbon-equivalent concentration of the particular hydrocarbon as the combustible-gas concentration $p_{THC}$, the particular hydrocarbon being defined as the one or more kinds of hydrocarbons, excluding alkanes, among hydrocarbons having 3 or more carbon atoms. This can derive more appropriate constants.

In each of substeps (a1) and (a2), because a gas containing only a single kind of hydrocarbon is used as a target gas, the target gas used in each of substeps (a1) and (a2) is easily prepared. Thus, the constants $\alpha$, $\beta$, and B can be more easily derived.

The present invention is not limited to the above-described embodiment, and can be carried out by various modes as long as they belong to the technical scope of the invention.

For example, in the foregoing embodiment, although the detection electrode 51 and the reference electrode 53 are arranged on the solid electrolyte layer 44, the solid electrolyte layer 44 is not necessarily used, and they may be arranged on a solid electrolyte body. For example, the detection electrode 51 and the reference electrode 53 may be arranged on upper and lower surfaces of a solid electrolyte body including solid electrolyte layers stacked. In the foregoing embodiment, although the reference electrode 53 serves as both of the reference electrode of the mixed potential cell 55 and the reference electrode of the concentration cell 56, this structure is not necessarily used, and the mixed potential cell 55 and the concentration cell 56 may include different reference electrodes.

In the foregoing embodiment, although the sensor element 31 includes the concentration cell 56 and thus can measure the oxygen concentration, this structure is not necessarily used. The sensor element 31 may not include the concentration cell 56 (specifically, the auxiliary electrode 52). In this case, the apparatus 70 for measuring combustible gas concentration may acquire information about the oxygen concentration from other than the sensor element 31. For example, the apparatus 70 for measuring combustible gas concentration may acquire information about the oxygen concentration from another sensor that is arranged in the exhaust gas path 3 and that can detect information about the oxygen concentration (for example, an oxygen sensor, an A/F sensor, or a NOx sensor). The apparatus 70 for measuring combustible gas concentration may acquire information about the oxygen concentration from another device (such as the engine ECU 9) other than sensors. In the case where the apparatus 70 for measuring combustible gas concentration acquires information about the oxygen concentration from another sensor arranged at a position of the exhaust gas path 3, the position being different from that of the sensor element 31, the apparatus 70 for measuring combustible gas concentration preferably derives the combustible gas concentration in consideration of a measurement time lag (time lag C) the difference in position between the sensor element 31 and due to the another sensor attached. Specifically, letting the length of time that the target gas flow from the position of one, located upstream, of the sensor element 31 and the another sensor to the position of the other in the exhaust gas path 3 be the time lag C, the apparatus 70 for measuring combustible gas concentration preferably derives the combustible gas concentration in consideration of the time lag C. For example, in the case where the another sensor is located on the upstream side of the sensor element 31, the control section 72 allows the memory part 73 to store the values of oxygen concentration acquired from the another sensor every predetermined period during the time lag C. Every time the electromotive force EMF is acquired from the sensor element 31, the control section 72 reads the oldest value of oxygen concentration at that time (=value acquired in the past by the time lag C) from the memory part 73 and derives the combustible gas concentration from the acquired electromotive force EMF, the value of the oxygen concentration read, and formula (1). In this way, the apparatus 70 for measuring combustible gas concentration can derive the combustible gas concentration with higher accuracy by considering the time lag C.

Although the engine 1 is a diesel engine in the foregoing embodiment, a gasoline engine may be used.

In the foregoing embodiment, although the apparatus 70 for measuring combustible gas concentration is an apparatus different from the engine ECU 9, the apparatus 70 for measuring combustible gas concentration may be part of the engine ECU 9.

EXAMPLES

Examples in which a method for deriving a constant and a method for measuring combustible-gas concentration were specifically performed will be described as Examples. The present invention is not limited to Examples described below.

[Study of Hydrocarbon Concentration in Exhaust Gas of engine]

Figure 6:
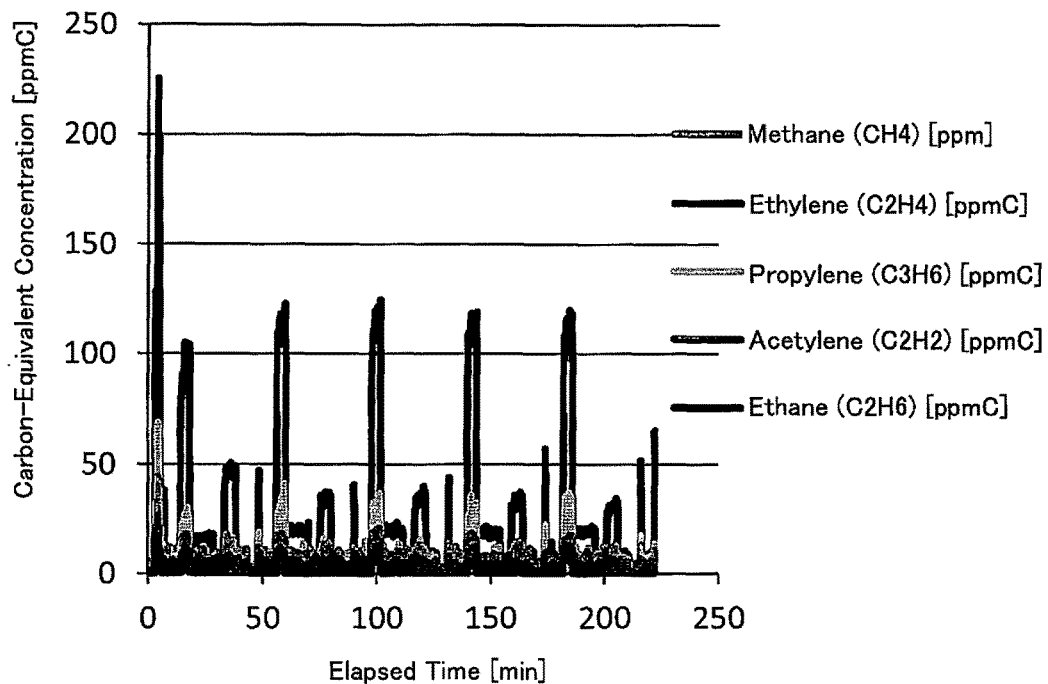
FIG. 6 is a graph depicting the relationship between elapsed engine operating time and the carbon-equivalent concentrations of various hydrocarbons in an exhaust gas.
Figure 7:
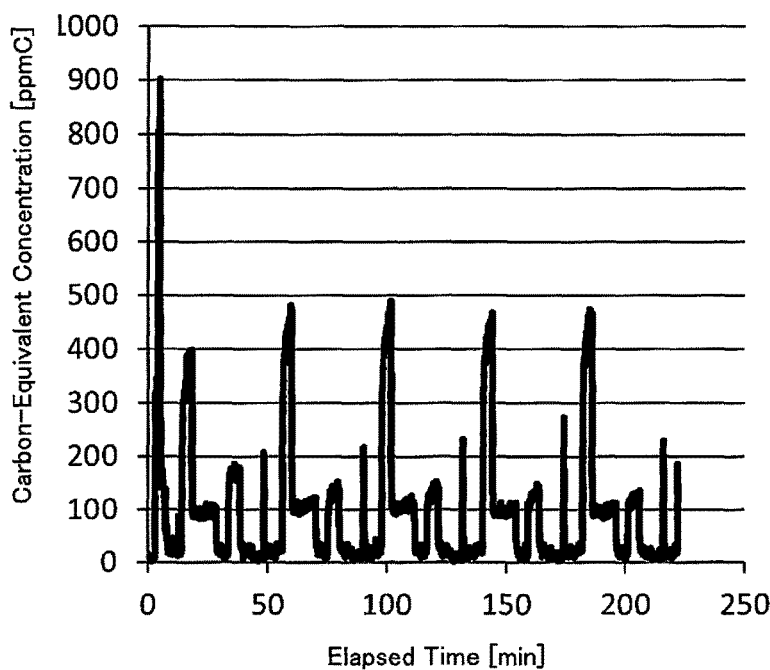
FIG. 7 is a graph depicting the relationship between the elapsed engine operating time and the carbon-equivalent concentration of all hydrocarbons in the exhaust gas.

An FT-IR analyzer (FAST 3000, manufactured by Iwata Dengyo Co., Ltd.) was connected to an exhaust pipe of a 2 L diesel engine. The diesel engine was subjected to a cycle operation in this state, and the resulting exhaust gas was analyzed to obtain FIGS. 6 and 7. FIG. 6 is a graph depicting the relationship between elapsed engine operating time [min] and the carbon-equivalent concentrations [ppmC] of methane ($CH_4$), ethylene ($C_2H_4$), propylene ($C_3H_6$), acetylene ($C_2H_2$), and ethane ($C_2H_6$) in the exhaust gas. FIG. 7 is a graph depicting the relationship between the elapsed engine operating time [min] and the carbon-equivalent concentration of all hydrocarbons in the exhaust gas. FIG. 6 indicates that the proportion of $C_2H_4$ among $CH_4$, $C_2H_4$, $C_3H_6$, $C_2H_2$, and $C_2H_6$ in the exhaust gas was relatively high. However, comparisons of FIG. 6 with FIG. 7 indicate that even the proportion of $C_2H_4$ in all hydrocarbons in the exhaust gas was about 20%, which is relatively low. From these results, it is anticipated that the exhaust gas has high proportions of hydrocarbons other than five hydrocarbons described in FIG. 6, in other words, has high proportions of hydrocarbons having a high molecular weight, which are difficult to identify with the FT-IR analyzer. It is thus conceivable that the concentrations of these hydrocarbons having a high molecular weight significantly affect the electromotive force EMF of the sensor element.

[Production of Sensor Elements 1 and 2]

A sensor element to be used for the measurement of combustible-gas concentration with an apparatus for measuring combustible-gas concentration was produced. Four non-fired ceramic green sheets containing a ceramic component composed of a zirconia solid electrolyte containing 3% by mole yttria serving as a stabilizer were prepared as the layers of the base 40. For example, sheet holes used for positioning during printing and stacking and through-holes required were formed in the green sheets, in advance. A space to be formed into the reference gas introduction cavity 46 was formed in the green sheet to be formed into the spacer layer 43 by, for example, punching, in advance. Various patterns were formed by pattern printing on each of the ceramic green sheets corresponding to the first substrate layer 41, the second substrate layer 42, the spacer layer 43, and the solid electrolyte layer 44, and the resulting ceramic green sheets were subjected to drying treatment. Specifically, for example, patterns for the detection electrode 51 composed of the Au—Pt alloy, the auxiliary electrode 52 and the reference electrode 53 composed of Pt, lead wires, and the heater portion 60 were formed. The pattern printing was performed by applying pattern-forming pastes to the green sheets using a known screen printing technique, each of the pattern-forming pastes being prepared to provide characteristics required for a corresponding one of the target objects. After the pattern printing and the drying were completed, printing and drying treatment of a bonding paste to stack and bond the green sheets corresponding to the layers together were performed. Compression bonding treatment was performed in which the green sheets including the bonding paste were stacked in a predetermined order while the green sheets were positioned with the sheet holes, and the resulting stack were subjected to compression bonding under predetermined temperature and pressure conditions to form a laminate. The resulting laminate was cut into laminated pieces having the same size as the sensor element 31. The resulting laminated pieces were fired with a tubular furnace at 1,100° C. for 2 hours in an air atmosphere, thereby providing the sensor elements 31 each including the detection electrode 51, the auxiliary electrode 52, and the reference electrode 53 that were arranged on the solid electrolyte layer 44. The sensor elements 31 were subjected to dipping with an alumina-containing slurry and firing to form the porous protective layers 48 on surfaces of the sensor elements 31. In this way, each of the sensor elements 31 was produced and was referred to as a sensor element 1. After the formation of a fracture surface of the detection electrode 51, the degree of concentration on noble-metal surfaces of the detection electrode 51 of the sensor element 1 was measured by AES and found to be 1.09. The porous protective layer 48 had a porosity of 40%. A sensor element 2 was produced in the same way as the sensor element 1, except that the detection electrode 51 had a degree of concentration of 0.99 and that the porous protective layer 48 had a porosity of 28%. In the following tests, the operating temperature of the sensor elements 1 and 2 in use was 600° C.

Experiment 1: Examination of Sensitivity of Alkane to Electromotive Force EMF

Figure 8:
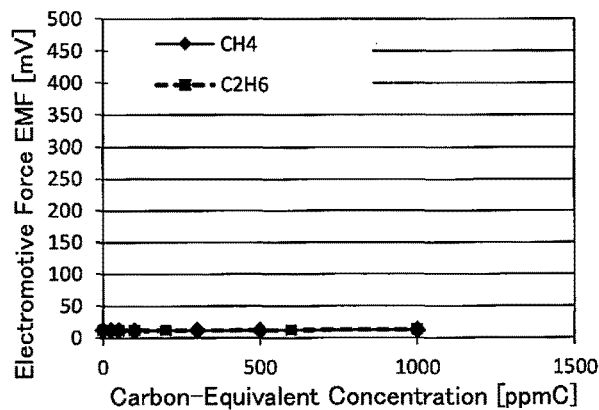
FIG. 8 is a graph depicting the relationship between the carbon-equivalent concentrations of alkanes and the electromotive force EMF of a sensor element 1.

Target gases each containing a mixture of oxygen, $H_2O$, methane ($CH_4$) serving as a combustible gas, and nitrogen serving as a base gas were prepared. The electromotive force EMF of the mixed potential cell 55 of the sensor element 1 was measured while the sensor element 1 was exposed to the target gases. The target gases had a constant oxygen concentration $p_{O2}$ of 10%, a constant $H_2O$ concentration $p_{H2O}$ of 5%, and different carbon-equivalent concentrations of $CH_4$ as listed in Table 1. A component other than these components in the target gas was nitrogen. The temperature was 120° C. The target gas was allowed to flow through the pipe having a diameter of 70 mm at a flow rate of 5 L/min. Similarly, the electromotive force EMF was measured with ethane ($C_2H_6$) serving as a combustible gas at different carbon-equivalent concentrations of $C_2H_6$ as listed in Table 1. Table 1 and FIG. 8 illustrate the results. FIG. 8 is a graph depicting the relationship between the carbon-equivalent concentrations [ppmC] of alkanes and the electromotive force EMF [mV] of the sensor element 1. Table 1 and FIG. 8 indicated that the carbon-equivalent concentrations of the alkanes in the target gas had little effect on the electromotive force EMF and that the electromotive force EMF remained substantially unchanged at different carbon-equivalent concentrations (the alkanes had little sensitivity to the electromotive force EMF). In experiment 1, $CH_4$ or $C_2H_6$ was used as alkane. Alkanes having 3 or more carbon atoms also seem to have the same tendency. It is thus believed that when the constants α, β, and B in formula (1) are derived, a gas containing a hydrocarbon other than alkanes is preferably used as a target gas.

TABLE 1

| Carbon-Equivalent Concentration [ppmC] ($CH_4$) | EMF [mV] | Carbon-Equivalent Concentration [ppmC] ($C_2H_8$) | EMF [mV] |
| --- | --- | --- | --- |
| 0 | 11.8 | 0 | 11.4 |
| 25 | 11.9 | 50 | 11.2 |
| 50 | 11.7 | 100 | 11.8 |
| 100 | 11.5 | 200 | 11.3 |
| 300 | 11.8 | 600 | 12 |
| 500 | 11.6 | 1000 | 12.9 |
| 1000 | 12.1 | | |

Figure 9:
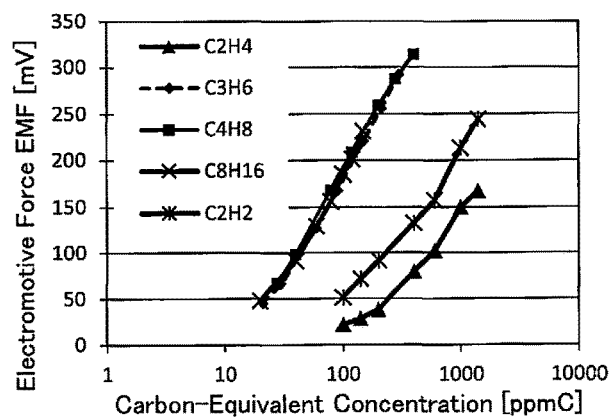
FIG. 9 is a graph depicting the relationship between the carbon-equivalent concentrations of alkenes and an alkyne and the electromotive force EMF of the sensor element 2.

Experiment 2: Examination of Sensitivity of Alkene and Alkyne to Electromotive Force EMF The electromotive force EMF was measured as in experiment 1, except that ethylene ($C_2H_4$) was used as the combustible gas in the target gas, different carbon-equivalent concentrations of $C_2H_4$ as listed in Table 2 were used, and the sensor element 2 was used. Similarly, the electromotive force EMF was measured in case that acetylene ($C_2H_2$), propylene ($C_3H_6$), butene ($C_4H_8$), or octene ($C_8H_{16}$) was used as the combustible gas and that different carbon-equivalent concentrations of these hydrocarbons as listed in Table 2 were used. Table 2 and FIG. 9 illustrate the results. FIG. 9 is a graph depicting the relationship between the carbon-equivalent concentrations [ppmC] of the alkenes and the alkyne and the electromotive force EMF of the sensor element 2. The horizontal axis of FIG. 9 is on a logarithmic scale. As is clear from Table 2 and FIG. 9, comparisons of $C_2H_4$ and $C_2H_2$, which are hydrocarbons having 2 carbon atoms, with the hydrocarbons having 3 or more carbon atoms indicated that the latter had a larger electromotive force EMF at the same carbon-equivalent concentration. That is, the degrees of effect (sensitivity) of the hydrocarbons having 3 or more carbon atoms on the electromotive force EMF of the mixed potential cell 55 were higher than those of the hydrocarbons having 2 carbon atoms. The alkenes having 3 or more carbon atoms had substantially the same relationship between the carbon-equivalent concentration and the electromotive force EMF. That is, the alkenes having 3 or more carbon atoms had substantially the same degree of effect (sensitivity) on the electromotive force EMF. It was found that in the case where the alkenes having 3 or more carbon atoms were used as the combustible gas and where the oxygen concentration $p_{O2}$ was fixed, the relationship between the logarithm of the combustible-gas concentration $p_{THC}$ and the electromotive force EMF can be approximated by a straight line. Comparisons of $C_2H_4$, which is an alkene, with $C_2H_2$, which is an alkyne, both having the same number of carbon atoms, indicated that the degree of effect (sensitivity) of the alkyne on the electromotive force EMF of the mixed potential cell 55 was higher than that of the alkene. The results of experiments 1 and 2 indicated that the degrees of effect (sensitivity) of the alkenes, excluding alkanes, having 3 or more carbon atoms on the electromotive force EMF of the mixed potential cell 55 were higher than those of hydrocarbons having 2 or less carbon atoms. Accordingly, it is conceivable that when the constants α, β, and B in formula (1) are derived, a gas containing an alkene having 3 or more carbon atoms is preferably used as a target gas. From the results of experiments 1 and 2, it is assumed that the degrees of effect (sensitivity) of alkenes having 3 or more carbon atoms and so forth, excluding alkanes, on the electromotive force EMF of the mixed potential cell 55 and the degrees of effect (sensitivity) of hydrocarbons, excluding alkanes, having 3 or more carbon atoms on the electromotive force EMF of the mixed potential cell 55 are higher than those of hydrocarbons having 2 or less carbon atoms.

[Derivation of Constant α]

The correspondence between the carbon-equivalent concentration and the electromotive force EMF in the case of using $C_3H_6$ as the combustible gas in experiment 2 was used as the first electromotive force data sets in substep S200 of the constant derivation processing. The carbon-equivalent concentration of $C_3H_6$ in the first electromotive force data sets was regarded as the combustible-gas concentration $p_{THC}$, and the processing in substep S210 was executed to derive the constant α of formula (1). Specifically, an approximate straight line expressing the correspondence between the combustible-gas concentration $p_{THC}$ and the electromotive force EMF in the case of using $C_3H_6$ as the combustible gas was determined (formula (3) described below). The constant α of the sensor element 2 was derived from the slope of this approximate straight line and found to be 94.91. The units of the combustible-gas concentration $p_{THC}$ in formula (3) were [ppmC].

$$EMF = 94.91 \ln(p_{THC}) - 248.84 \quad (3)$$

Experiment 3: Examination of Sensitivity of Oxygen to Electromotive Force EMF

Figure 10:
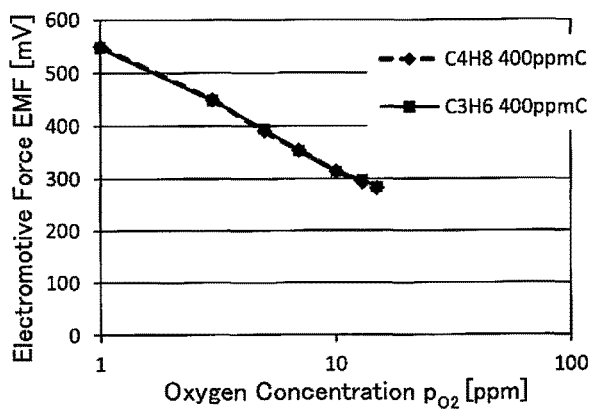
FIG. 10 is a graph depicting the relationship between the oxygen concentration $p_{O2}$ and the electromotive force EMF of the sensor element 2.

The electromotive force EMF was measured as in experiment 1, except that $C_3H_6$ was used as the combustible gas in the target gas, the carbon-equivalent concentration of $C_3H_6$ was fixed to 400 ppmC, the $H_2O$ concentration $p_{H2O}$ was fixed to 5%, different oxygen concentrations $p_{O2}$ as listed in Table 3 were used, and the sensor element 2 was used. Furthermore, the electromotive force EMF was similarly measured, except that $C_4H_8$ (carbon-equivalent concentration: 400 ppmC) was used as the combustible gas and different oxygen concentrations $p_{O2}$ as listed in Table 3 were used. Table 3 and FIG. 10 illustrate the results. FIG. 10 is a graph depicting the relationship between the oxygen concentration $p_{O2}$ [%] and the electromotive force EMF [mV] of the sensor element 2. The horizontal axis of FIG. 10 is on a logarithmic scale. Table 3 and FIG. 10 indicated that the relationship between the logarithm of the oxygen concentration $p_{O2}$ and the electromotive force EMF at a constant combustible-gas concentration $p_{THC}$ could be approximated by a straight line. There was substantially no difference in the relationship regardless of whether the combustible gas was $C_3H_6$ or $C_4H_8$. From this result, it is conceivable that any hydrocarbon may be used as the combustible gas used to acquire the second electromotive force data sets at different oxygen concentrations of formula (1).

TABLE 2

| Carbon-Equivalent Concentration [ppmC] ($C_2H_4$) | EMF [mV] | Carbon-Equivalent Concentration [ppmC] ($C_2H_2$) | EMF [mV] | Carbon-Equivalent Concentration [ppmC] ($C_3H_5$) | EMF [mV] | Carbon-Equivalent Concentration [ppmC] ($C_4H_8$) | EMF [mV] | Carbon-Equivalent Concentration [ppmC] ($C_8H_{16}$) | EMF [mV] |
|---|---|---|---|---|---|---|---|---|---|
| 0 | 11.3 | 0 | 11.4 | 0 | 11.4 | 0 | 15.7 | 0 | 11.5 |
| 100 | 21.9 | 100 | 51.3 | 21 | 45.4 | 28 | 67.1 | 20 | 48.1 |
| 140 | 28.4 | 140 | 71.4 | 30 | 65.8 | 40 | 98.2 | 40 | 91.3 |
| 200 | 37.9 | 200 | 91.5 | 60 | 127 | 80 | 167.5 | 60 | 129.1 |
| 400 | 79.5 | 400 | 132.7 | 90 | 167.1 | 120 | 208.3 | 80 | 155.7 |
| 600 | 102.4 | 600 | 157.1 | 150 | 220.4 | 200 | 258.9 | 100 | 184.7 |
| 1000 | 150.3 | 1000 | 213.1 | 210 | 255.1 | 280 | 287.3 | 120 | 200.8 |
| 1400 | 167.5 | 1400 | 243.8 | 300 | 291.9 | 400 | 313.8 | 148 | 231.1 |

TABLE 3

| $P_{O2}$ [%] | (C$_3$H$_6$) EMF [mV] | (C$_4$H$_8$) EMF [mV] |
|---|---|---|
| 1 | 547.6 | 549.6 |
| 3 | 448.4 | 449.6 |
| 5 | 394.1 | 390.4 |
| 7 | 351.9 | 353 |
| 10 | 312.7 | 313.8 |
| 13 | 297.1 | 292.3 |
| 15 | 283.4 | 281.7 |

[Derivation Constant β]

The correspondence between the oxygen concentration $p_{O2}$ and the electromotive force EMF in the case of using C$_3$H$_6$ as the combustible gas in experiment 3 was used as the second electromotive force data sets in substep S220 of the constant derivation processing. The carbon-equivalent concentration of C$_3$H$_6$ in the second electromotive force data sets was regarded as the combustible-gas concentration $p_{THC}$, and the processing in substep S230 was executed to derive the constant β of formula (1). Specifically, an approximate straight line expressing the correspondence between the oxygen concentration $p_{O2}$ and the electromotive force EMF in the case of using C$_3$H$_6$ as the combustible gas was determined (formula (4) described below). The constant β of the sensor element 2 was derived from the slope of this approximate straight line and found to be 99.91. The oxygen concentration $p_{O2}$ in formula (4) was dimensionless (for example, in the case of 10%, a value of 0.1).

$$\text{EMF} = -99.91 \ln(p_{O2}) + 551 \quad (4)$$

[Derivation of Constant B]

The constant B of the sensor element 2 was derived from the data sets obtained in the case of using C$_3$H$_6$ as the combustible gas in experiments 2 and 3. The constant B was derived as the average of the constants B derived from the first electromotive force data sets obtained in experiment 2 and the constants B derived from the second electromotive force data sets obtained in experiment 3. As a result, the constant B of the sensor element 2 was derived and found to be −478.89.

From the results described above, formula (5) that expresses the relationship among the variables (EMF, $p_{THC}$, and $p_{O2}$) of the sensor element 2 was derived. In formula (5), each of the bases a and b in formula (1) is Napier's constant e. In formula (5), the units of the electromotive force EMF are [mV], the units of the combustible-gas concentration $p_{THC}$ are [ppm], and the oxygen concentration $p_{O2}$ are dimensionless (for example, in the case of 10%, a value of 0.1).

$$\text{EMF} = 94.91 \ln(p_{THC}) - 99.91 \ln(p_{O2}) - 478.89 \quad (5)$$

Experiment 4: Evaluation Test

Figure 11:
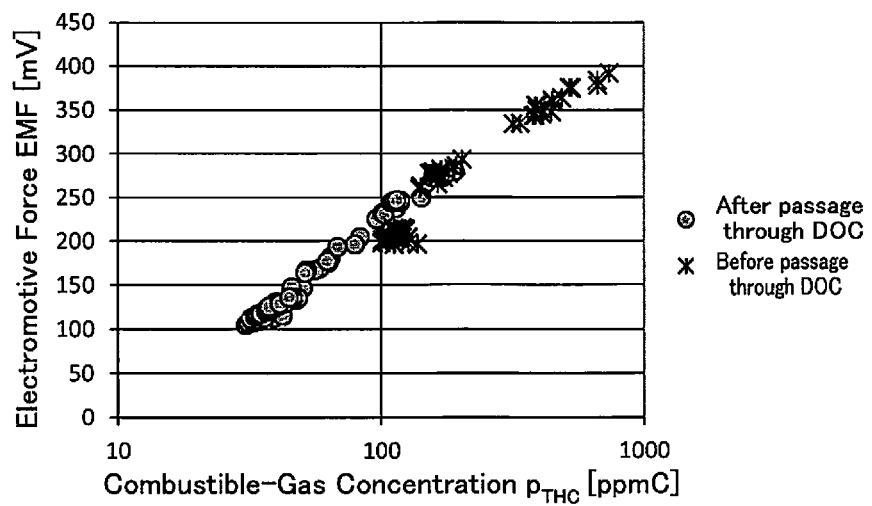
FIG. 11 is a graph depicting the correspondence relationship between the measured combustible-gas concentration $p_{THC}$ and the measured electromotive force EMF.

The combustible-gas concentration $p_{THC}$ in an exhaust gas of an actual engine and the electromotive force EMF of the sensor element 2 were measured, and comparisons of the results with formula (5) were made. A DOC was connected to an exhaust pipe of a 2 L diesel engine. The diesel engine was operated in a steady state, and the oxygen concentration $p_{O2}$ in the exhaust gas was fixed to 7.5%. The combustible-gas concentration $p_{THC}$ in the exhaust gas was changed by changing the amount of fuel injected in the post injection (last injection in multi-stage injection) of the diesel engine. In the case where the combustible-gas concentration $p_{THC}$ was changed with time as described above, the combustible-gas concentration $p_{THC}$ in the exhaust gas to be passed through the DOC was actually measured with an FID at each time, and the electromotive force EMF of the sensor element 2 was actually measured at each time while the sensor element 2 was exposed to the exhaust gas to be passed through the DOC. After the exhaust gas was passed through the DOC, similarly, the combustible-gas concentration $p_{THC}$ and the electromotive force EMF were actually measured with the FID and the sensor element 2. FIG. 11 is a graph depicting the correspondence between the measured combustible-gas concentration $p_{THC}$ and the measured electromotive force EMF. In FIG. 11, data obtained from the exhaust gas to be passed through the DOC and data obtained from the exhaust gas that had been passed through the DOC are separately illustrated. The horizontal axis in FIG. 11 is on a logarithmic scale. An approximate straight line expressing the correspondence between the measured combustible-gas concentration $p_{THC}$ and the measured electromotive force EMF illustrated in FIG. 11 was determined without separating the data sets before and after the passage through the DOC and was represented by formula (6). By substituting the oxygen concentration $p_{O2}=0.075$ (=7.5%) in formula (5) derived above, formula (5)' was obtained. It was found that formula (6) was substantially matched to formula (5)'. That is, it was found that formula (5) derived from formula (1) was substantially matched to formula (6) based on the measured values. It was thus found that the combustible-gas concentration in the target gas could be derived from formula (1) with high accuracy. It was also found that even in the case where a hydrocarbon having 3 or more carbon atoms (alkene having 3 or more carbon atoms, such as C$_3$H$_6$) was used as a particular hydrocarbon without using an exhaust gas of an actual engine and where the coefficients α, β, and B in formula (1) were derived by regarding the carbon-equivalent concentration of the particular hydrocarbon as the combustible-gas concentration $p_{THC}$, appropriate coefficients α, β, and B could be derived.

$$\text{EMF} = 94.845 \ln(p_{THC}) - 224.08 \quad (6)$$

$$\text{EMF} = 94.91 \ln(p_{THC}) - 220.10 \quad (5)'$$

Experiments 5 and 6: Examination of H$_2$O Interference and CO$_2$ Interference

Figure 12:
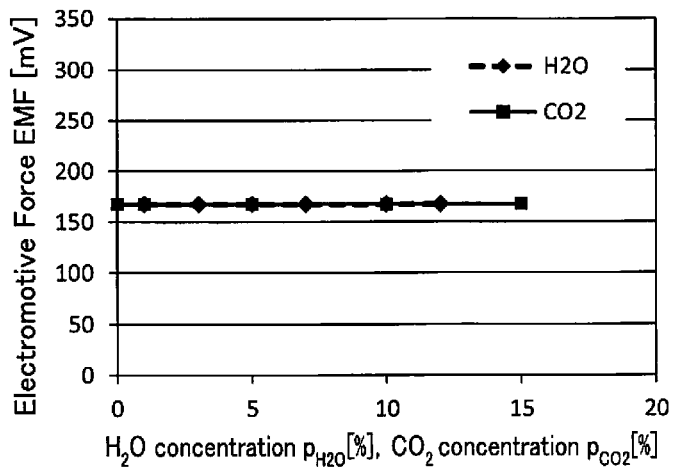
FIG. 12 is a graph depicting the relationship between the $H_2O$ concentration $p_{H2O}$ or the $CO_2$ concentration $p_{CO2}$ and the electromotive force EMF.

The electromotive force EMF was measured as in experiment 1, except that C$_3$H$_6$ was used as the combustible gas in the target gas, the carbon-equivalent concentration of C$_3$H$_6$ was fixed to 90 ppmC, the oxygen concentration $p_{O2}$ was fixed to 10%, different H$_2$O concentrations $p_{H2O}$ as listed in Table 4 were used, and the sensor element 2 was used (experiment 5). Furthermore, the electromotive force EMF was measured as in experiment 5, except that the H$_2$O concentration $p_{H2O}$ was fixed to 5% and different CO$_2$ concentrations $p_{CO2}$ as listed in Table 4 were used (experiment 6). FIG. 12 is a graph depicting the relationship between the H$_2$O concentration $p_{H2O}$ [%] or the CO$_2$ concentration $p_{CO2}$ [%] and the electromotive force EMF [mV] of the sensor element 2. Table 4 and FIG. 12 indicated that the electromotive force EMF remained substantially unchanged at different H$_2$O concentrations $p_{H2O}$ in the target gas (substantially no H$_2$O interference). It was also found that the electromotive force EMF remained substantially unchanged at different CO$_2$ concentrations $p_{CO2}$ in the target gas (substantially no CO$_2$ interference). That is, it was found that the term in the H$_2$O concentration $p_{H2O}$ and the term in the CO$_2$ concentration $p_{CO2}$ in formula (2) were not matched to the actual relationship among the electromotive force EMF, the H₂O concentration $p_{H2O}$, and the CO₂ concentration $p_{CO2}$.

TABLE 4

| $p_{H2O}$ [%] | EMF [mV] | $p_{CO2}$ [%] | EMF [mV] |
|---|---|---|---|
| 1 | 167.2 | 0 | 167.1 |
| 3 | 167.1 | 1 | 167.2 |
| 5 | 167.1 | 5 | 167.1 |
| 7 | 167.1 | 10 | 167.1 |
| 10 | 167.1 | 15 | 167.1 |
| 12 | 167.1 | | |

What is claimed is:

1. An apparatus for measuring combustible-gas concentration serving as carbon-equivalent concentration of a combustible gas in a target gas with a sensor element including a mixed potential cell that includes a solid electrolyte body, a detection electrode arranged on the solid electrolyte body, and a reference electrode arranged on the solid electrolyte body, the apparatus comprising:
    an electromotive force acquisition section configured to acquire information about an electromotive force of the mixed potential cell while the detection electrode is exposed to the target gas;
    an oxygen concentration acquisition section configured to acquire information about oxygen concentration in the target gas; and
    a combustible gas concentration derivation section configured to determine the combustible-gas concentration in the target gas based on the acquired information about the electromotive force, the acquired information about the oxygen concentration, and a relationship represented by formula (1):

$$\text{EMF} = \alpha \log_a(p_{THC}) - \beta \log_b(p_{O2}) + B \quad (1)$$

(where
    EMF: the electromotive force of the mixed potential cell,
    α, β, and B: constants,
    a and b: any base (provided that a≠1, a>0, b≠1, and b>0),
    $p_{THC}$: the combustible-gas concentration in the target gas, and
    $p_{O2}$: the oxygen concentration in the target gas).

2. A system for measuring combustible-gas concentration, comprising:
    apparatus for measuring combustible-gas concentration according to claim 1; and
    the sensor element.

3. The system for measuring combustible-gas concentration according to claim 2,
    wherein the detection electrode is composed of a Au—Pt alloy as a main component.

4. The system for measuring combustible-gas concentration according to claim 3,
    wherein the detection electrode has a degree of concentration (=amount of Au present [atom %]/amount of Pt present [atom %]) of 0.3 or more, the degree of concentration being measured by at least one of X-ray photoelectron spectroscopy (XPS) and Auger electron spectroscopy (AES).

5. The system for measuring combustible-gas concentration according to claim 2,
    wherein the sensor element includes a heater configured to heat the mixed potential cell to an operating temperature of 450° C. or higher and 600° C. or lower.

6. The system for measuring combustible-gas concentration according to claim 2,
    wherein the sensor element includes a protective layer that covers the detection electrode, the protective layer having a porosity of 28% or more by volume.

7. A system for treating an exhaust gas, comprising:
    the system for measuring combustible-gas concentration according to claim 2; and
    an exhaust gas path through which an exhaust gas serving as the target gas from an internal combustion engine flows, the sensor element being arranged in the exhaust gas path.

8. The system for treating an exhaust gas according to claim 7, further comprising:
    one or more supply sections arranged in the exhaust gas path, the one or more supply sections being configured to supply at least one of urea and ammonia,
    wherein the internal combustion engine is a diesel engine, and
    the sensor element is arranged upstream of the most upstream supply section of the one or more supply sections arranged in the exhaust gas path.

9. A method for measuring combustible-gas concentration serving as a carbon-equivalent concentration of a combustible gas in a target gas with a sensor element including a mixed potential cell that includes a solid electrolyte body, a detection electrode arranged on the solid electrolyte body, and a reference electrode arranged on the solid electrolyte body, the method comprising:
    an electromotive force acquisition step of acquiring information about an electromotive force of the mixed potential cell while the detection electrode is exposed to the target gas;
    an oxygen concentration acquisition step of acquiring information about oxygen concentration in the target gas; and
    a combustible gas concentration derivation step of determining the combustible-gas concentration in the target gas based on the acquired information about the electromotive force, the acquired information about the oxygen concentration, and a relationship represented by formula (1):

$$\text{EMF} = \alpha \log_a(p_{THC}) - \beta \log_b(p_{O2}) + B \quad (1)$$

(where
    EMF: the electromotive force of the mixed potential cell,
    α, β, B: constants,
    a and b: any base (provided that a≠1, a>0, b≠1, and b>0),
    $p_{THC}$: the combustible-gas concentration in the target gas, and
    $p_{O2}$: the oxygen concentration in the target gas).

10. A method for deriving a constant in a relational formula used to measure combustible-gas concentration serving as carbon-equivalent concentration of a combustible gas in a target gas with a sensor element including a mixed potential cell that includes a solid electrolyte body, a detection electrode arranged on the solid electrolyte body, and a reference electrode arranged on the solid electrolyte body, the method comprising:
    (a) a step of multiple times of executing electromotive force measurement processing that measures an electromotive force of the mixed potential cell in a state in which the detection electrode is exposed to the target gas while at least one of oxygen concentration and the carbon-equivalent concentration of at least one combustible gas of one or more combustible gases in the target gas is changed, a gas containing oxygen and the one or more combustible gases being used as the target gas; and (b) a step of deriving constants α, β, and B in formula (1) from results of the electromotive force measurement processing executed multiple times:

$$EMF = \alpha \log_a(p_{THC}) - \beta \log_b(p_{O2}) + B \quad (1)$$

(where

EMF: the electromotive force of the mixed potential cell,

α, β, and B: constants, a and b: any base (provided that a≠1, a>0, b≠1, and b>0), $p_{THC}$: the combustible-gas concentration in the target gas, and $p_{O2}$: the oxygen concentration in the target gas).

11. The method for deriving a constant according to claim 10, wherein step (a) includes:
(a1) a substep of executing the electromotive force measurement processing multiple times at a constant oxygen concentration and different carbon-equivalent concentrations of a particular hydrocarbon in the target gas, the particular hydrocarbon being defined as one or more kinds of hydrocarbons, excluding alkanes, among hydrocarbons having 3 or more carbon atoms, and the target gas being defined as a gas containing the particular hydrocarbon; and
(a2) a substep of executing the electromotive force measurement processing multiple times at a constant carbon-equivalent concentration of a particular hydrocarbon and different oxygen concentrations in the target gas, the particular hydrocarbon being defined as one or more kinds of hydrocarbons, excluding alkanes, among hydrocarbons having 3 or more carbon atoms, and the target gas being defined as a gas containing the particular hydrocarbon, and step (b) includes:
(b1) a substep of deriving the constant α in formula (1) from the results of the electromotive force measurement processing executed multiple times in substep (a1) by regarding the carbon-equivalent concentration of the particular hydrocarbon as the combustible-gas concentration $p_{THC}$;
(b2) a substep of deriving the constant β in formula (1) from the results of the electromotive force measurement processing executed multiple times in substep (a2) by regarding the carbon-equivalent concentration of the particular hydrocarbon as the combustible-gas concentration $p_{THC}$; and
(b3) a substep of deriving the constant B in formula (1) from the derived constants α and β and the results of the electromotive force measurement processing executed one or more times in at least one of substeps (a1) and (a2).

12. The method for deriving a constant according to claim 11, wherein in substep (a1), the particular hydrocarbon comprises one or more kinds of hydrocarbons among hydrocarbons that have 3 or more carbon atoms, that have a double bond, and that do not have a triple bond, and in substep (a2), the particular hydrocarbon comprises one or more kinds of hydrocarbons among hydrocarbons that have 3 or more carbon atoms, that have a double bond, and that do not have a triple bond.

13. The method for deriving a constant according to claim 11, wherein in substep (a1), the target gas is a gas containing only a single kind of hydrocarbon, and in substep (a2), the target gas is a gas containing only a single kind of hydrocarbon.

* * * * *